United States Patent [19]

Jäger et al.

[11] Patent Number: 4,562,185
[45] Date of Patent: Dec. 31, 1985

[54] FIVE-MEMBERED NITROGEN-CONTAINING HETERO-CYCLIC COMPOUNDS AND THEIR USE AS PEST-COMBATING AGENTS

[75] Inventors: Gerhard Jäger, Leverkusen; Rudolf Fauss, Cologne; Kurt Findeisen, Odenthal; Benedikt Becker, Mettmann; Bernhard Homeyer, Leverkusen, all of Fed. Rep. of Germany

[73] Assignee: Bayer Aktiengesellschaft, Leverkusen, Fed. Rep. of Germany

[21] Appl. No.: 589,985

[22] Filed: Mar. 15, 1984

[30] Foreign Application Priority Data

Mar. 30, 1983 [DE] Fed. Rep. of Germany ....... 3311636

[51] Int. Cl.$^4$ .................. A01N 43/82; C07D 291/04
[52] U.S. Cl. .................................. 514/229; 260/936;
514/63; 514/84; 514/86; 514/89; 514/90;
514/92; 514/93; 514/94; 514/95; 514/99;
514/110; 514/241; 514/256; 514/342; 514/360;
544/22; 544/69; 544/133; 544/157; 544/214;
544/216; 544/229; 544/243; 544/335; 546/14;
546/280; 548/110; 548/119; 548/122; 549/4;
549/6; 549/214; 549/218; 556/408
[58] Field of Search .................. 548/122; 546/280;
544/216, 335, 69, 133; 424/248.51, 249, 251,
263, 269, 270, 272, 273 R; 514/229, 241, 256,
342, 360

[56] References Cited

FOREIGN PATENT DOCUMENTS 0028752  5/1981  European Pat. Off. .
2315922  1/1977  France .

OTHER PUBLICATIONS

Chemical Abstracts, vol. 83, Aug. 18, 1975, I. V. Konovalova et al., p. 495, Abstract No. 58723t.
Zeitschrift fur Anorganische und Allgemeine Chemie, vol. 406, 1974, Leipzig, DDR. H. Steinbeisser et al., pp. 299–306, Formula 5.
Chemical Abstracts, vol. 83, Nov. 24, 1975, V. V. Dovlatyan et al., pp. 566–567, Abstract No. 178938p.
Chemical Abstracts, vol. 86, Apr. 11, 1977, V. V. Dovlatyan et al., p. 502, Abstract No. 106492c.
J. Org. Chem., vol. 42, No. 6, 1977, J. A. Deyrup et al., pp. 1015–1018, Formula 3.
Pharmaceuticals, Abstract, Week Y/15, p. 3; Publ. 2315922, 1977.
J. Gen. Chem. USSR vol. 43, pp. 256–260, Feb. 1973.

*Primary Examiner*—Richard L. Raymond
*Attorney, Agent, or Firm*—Sprung Horn Kramer & Woods

[57] ABSTRACT

The present invention relates to combating pests with five-membered nitrogen-containing heterocyclic compounds of the formula (I)

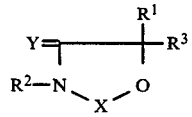

in which $R^1$, $R^2$, $R^3$, X and Y have the meaning given in the description. Many of the compounds are new.

6 Claims, No Drawings

FIVE-MEMBERED NITROGEN-CONTAINING HETERO-CYCLIC COMPOUNDS AND THEIR USE AS PEST-COMBATING AGENTS

The present invention relates to new five-membered nitrogen-containing heterocyclic compounds, processes for their preparation and their use as pest-combating agents.

1,2,3-Oxathiazolidin-4-ones are disclosed in French Patent Specification No. 2,315,922, Chemical Abstracts CA 86: 106492c. However, nothing concerning the properties of these compounds as pest-combating agents has been disclosed in this publication. 1,2,3-Oxazaphospholidine 2-oxides are disclosed in J. Gen. Chem. USSR Volume 43 I (1973), pages 256–259. However, nothing has been disclosed concerning the properties of these compounds as pest-combating agents.

It has already been disclosed that carbamates, such as 5,6-dimethyl-2-dimethylamino-pyrimidin-4-yl dimethylcarbamate or naphth-1-yl N-methylcarbamate, possess insecticidal activity (U.S. Pat. Nos. 3,493,574 and 2,903,478). However, their action is not always completely satisfactory, particularly when low concentrations are used.

1. The new five-membered nitrogen-containing heterocyclic compounds of the formula (I) have been found,

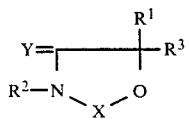

in which $R^1$ represents alkyl, alkenyl, alkinyl, cycloalkyl, cycloalkenyl, aryl and heteroaryl, which can be optionally substituted, $R^2$ represents hydrogen, one equivalent of an inorganic or organic cation or trialkylsilyl, and represents alkyl, cycloalkyl, alkenyl, alkinyl, aryl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl and arylalkylaminosulphonyl, which can be optionally substituted, and represents radicals of the formula $$-CO-NR^5R^6$$

wherein $R^5$ and $R^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted, $R^3$ represents alkyl, alkenyl, alkinyl, cycloalkyl, cycloalkenyl, aryl or heteroaryl, which are optionally substituted, and represents —CN and the radical

$R^4$ represents amino, —O—W, wherein W represents hydrogen, optionally substituted alkyl or cycloalkyl, aralkyl and one equivalent of an alkali metal or an alkaline earth metal, $R^4$ furthermore represents alkylamino, arylamino, aralkylamino, dialkylamino, cycloalkylamino, alkenylamino, trialkylsilylamino, trialkylsilylalkylamino, nitrogen-containing saturated heterocyclic radicals which optionally contain further heteroatoms, it being possible for the radicals to be substituted, $R^4$ furthermore represents radicals of the formula $$-NHR^7$$

wherein $R^7$ represents hydroxyl, formyyl, alkylcarbonyl, alkenylcarbonyl, cycloalkenylcarbonyl, arylcarbonyl, amino, alkylamino, arylamino, alkylarylamino, dialkylamino, alkylaminocarbonylamino

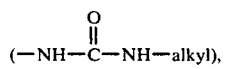

alkylaminothiocarbonylamino

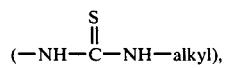

arylaminocarbonylamino, arylaminothiocarbonylamino, alkylcarbonylamino

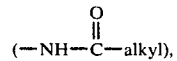

arylcarbonylamino, alkylsulphonylaminocarbonylamino

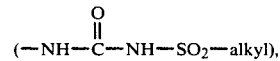

arylsulphonylaminocarbonylamino, alkylcarbonylaminocarbonylamino

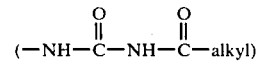

and arylcarbonylaminocarbonylamino, it being possible for the alkyl or aryl radicals to be optionally substituted, $R^4$ furthermore represents radicals of the formula

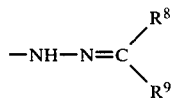

wherein $R^8$ represents alkyl or aryl, which can be optionally substituted, and $R^9$ represents hydrogen or alkyl, X represents S, SO, SO$_2$, >SiR$^{10}$R$^{11}$ or

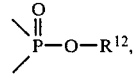

wherein
R$^{10}$ represents alkyl,
R$^{11}$ represents alkyl,
R$^{12}$ represents alkyl or aryl, and
Y represents O, S or =N—R$^{13}$,
wherein
R$^{13}$ represents alkyl or aryl, which can be optionally substituted;
if R$^1$ represents methyl or trifluoromethyl, R$^3$ cannot at the same time represent methyl or trifluoromethyl.

The five-membered nitrogen-containing heterocyclic compounds of the formula I occur in the form of mixtures of their steric and optical isomers as well as in the form of their pure isomers.

2. It has furthermore been found that the five-membered nitrogen-containing heterocyclic compounds of the formula I

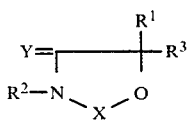

wherein
R$^1$ represents alkyl, alkenyl, alkinyl, cycloalkyl, cycloalkenyl, aryl and heteroaryl, which can be optionally substituted,
R$^2$ represents hydrogen, one equivalent of an inorganic or organic cation or trialkylsilyl, and represents alkyl, cycloalkyl, alkenyl, alkinyl, aryl, aralkyl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl and arylalkylaminosulphonyl, which can be optionally substituted, and represents radicals of the formula

—CO—NR$^5$R$^6$ wherein
R$^5$ and R$^6$ independently of one another represents hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted,
R$^3$ represents alkyl, alkenyl, alkinyl, cycloalkyl, cycloalkenyl, aryl or heteroaryl, which are optionally substituted, and represents —CN and the radical

R$^4$ represents amino, —QW, wherein W represents hydrogen, optionally substituted alkyl- or cycloalkyl, aralkyl and one equivalent of an alkali metal or an alkaline earth metal,
R$^4$ furthermore represents alkylamino, arylamino, aralkylamino, dialkylamino, cycloalkylamino, alkenylamino, trialkylsilylamino, trialkylsilylalkylamino, nitrogen-containing saturated heterocyclic radicals which optionally contain further heteroatoms, it being possible for the radicals to be substituted, R$^4$ furthermore represensts radicals of the formula

—NHR$^7$ wherein
R$^7$ represents hydroxyl, formyl, alkylcarbonyl, alkenylcarbonyl, cycloalkenylcarbonyl, arylcarbonyl, amino, alkylamino, arylamino, alkylarylamino, dialkylamino, alkylaminocarbonylamino

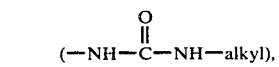

alkylaminothiocarbonylamino

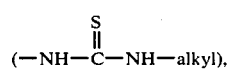

arylaminocarbonylamino, arylaminothiocarbonylamino, alkylcarbonylamino

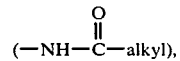

arylcarbonylamino, alkylsulphonylaminocarbonylamino

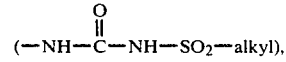

arylsulphonylaminocarbonylamino, alkylcarbonylaminocarbonylamino

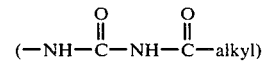

and arylcarbonylaminocarbonylamino, it being possible for the alkyl or aryl radicals to be optionally substituted,
R$^4$ furthermore represents radicals of the formula

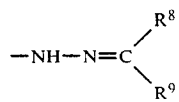

wherein
R$^8$ represents alkyl or aryl, which can be optionally substituted, and
R$^9$ represents hydrogen or alkyl,
X represents S, SO, SO$_2$, >SiR$^{10}$R$^{11}$ or

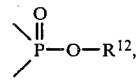

wherein
R$^{10}$ represents alkyl,
R$^{11}$ represents alkyl,
R$^{12}$ represents alkyl or aryl, and
Y represents O, S or =N—R$^{13}$,
wherein
R$^{13}$ represents alkyl or aryl, which can be optionally substituted;
if R$^1$ represents methyl or trifluoromethyl, R$^3$ cannot at the same time represent methyl or trifluoromethyl;
are obtained by a process in which (a) in the case in which it is intended to obtain compounds of the formula I in which X represents SO, S or $>SiR^{10}R^{11}$, compounds of the formula II

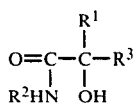  II in which $R^1$, $R^2$ and $R^3$ have the meaning given above, are reacted with compounds of the formula III $X^1Hal_2$  III in which Hal represents Halogen and $X^1$ represents SO, $>SiR^{10}R^{11}$ or S, and the resulting compounds are, if desired, treated with a base to form a salt, or (b) compounds of the formula IV

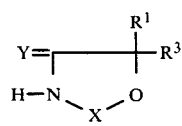  IV in which $R^1$, $R^3$, X and Y have the meaning given above, are reacted with compounds of the formula V $R^{14}-Z$  V in which $R^{14}$ represents trialkylsilyl, alkyl, cycloalkyl, alkenyl, alkinyl, aralkyl, aryl, alkylcarbonyl, arylcarbonyl, alkoxycarbonyl, aryloxycarbonyl, alkylsulphenyl, arylsulphenyl, alkylsulphonyl, arylsulphonyl, alkylaminosulphonyl, dialkylaminosulphonyl, arylaminosulphonyl or arylalkylaminosulphonyl, which can be optionally substituted, and represents radicals of the formula

—CO—NR$^5$R$^6$ wherein $R^5$ and $R^6$ independently of one another represent hydrogen, alkyl, cycloalkyl, aryl, alkylaminocarbonyl, arylaminocarbonyl, alkylcarbonyl, arylcarbonyl, alkoxycarbonyl, aryloxycarbonyl, alkylsulphonyl or arylsulphonyl, it being possible for these radicals to be optionally substituted, and Z represents a group which is reactive towards an acidic hydrogen atom, or (c) in the case in which it is intended to obtain compounds of the formula I in which X represents $>SiR^{10}R^{11}$, compounds of the formula II

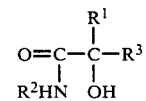  II in which $R^1$, $R^2$ and $R^3$ have the meaning given above (but $R^3$ cannot represent —COOH), are reacted with compounds of the formula IX

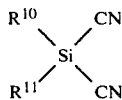  IX in which $R^{10}$ and $R^{11}$ have the meaning given above, and the resulting compounds are, if desired, treated with a base to form a salt, or (d) in the case in which it is intended to obtain compounds of the formula I in which X represents

and $R^2$ represents the radical $R^{12}$, compounds of the formula X $R^1-\overset{O}{\underset{\|}{C}}-\overset{O}{\underset{\|}{C}}-R^{16}$  X in which $R^1$ has the meaning given above and $R^{16}$ represents amino, alkylamino, arylamino, aralkylamino, dialkylamino, cycloalkylamino, alkenylamino, trialkylsilylamino, trialkylsilylalkylamino, nitrogen-containing saturated heterocyclic radicals which optionally contain further heteroatoms, it being possible for the radicals to be optionally subtituted, $R^4$ furthermore represents radicals of the formula

—NHR$^7$ wherein $R^7$ represents hydroxyl, formyl, alkylcarbonyl, alkenylcarbonyl, cycloalkenylcarbonyl, arylcarbonyl, amino, alkylamino, arylamino, alkylarylamino, dialkylamino, alkylaminocarbonylamino

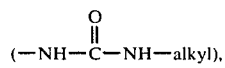

alkylaminocarbonylamion

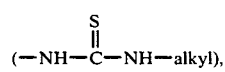

arylamionocarbonylamino, arylaminothiocarbonylamino, alkylcarbonylamino

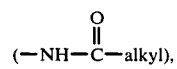

arylcarbonylamino, alkylsulphonylaminocarbonylamino

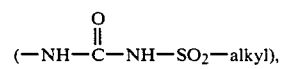

arylsulphonylaminocarbonylamino, alkylcarbonylaminocarbonylamino,

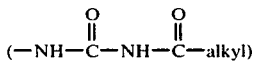

(—NH—C(=O)—NH—C(=O)—alkyl)

and arylcarbonylaminocarbonylamino, it being possible for the alkyl or aryl radicals to be optionally substituted, $R^{16}$ furthermore represents radicals of the formula

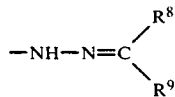

—NH—N=C(R⁸)(R⁹)

wherein $R^8$ represents alkyl or aryl which can be optionally substituted, and $R^9$ represents hydrogen or alkyl, are reacted with compounds of the formula XI

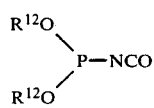

$(R^{12}O)_2 P$—NCO    XI in which $R^{12}$ has the meaning given above, or (e) in the case in which it is intended to obtain compounds of the formula I in which X represents >SO$_2$, compounds of the formula I in which X represents SO are reacted with oxidizing agents, such as peroxides and peracids.

Surprisingly, the five-membered nitrogen-containing heterocyclic compounds according to the invention have a substantially more powerful insecticidal action than the carbamates which are known from the state of the art and have the same direction of action, such as 5,6-dimethyl-2-dimethylamino-pyrimidin-4-yl dimethylcarbamate or naphth-1-yl N-methylcarbamate (U.S. Pat. No. 3,493,574 and U.S. Pat. No. 2,903,478).

Furthermore, the new five-membered nitrogen containing compounds possess a favorable level of toxicity and have a root-systemic action.

Preferred compounds of the formula I are those in which $R^1$ represents $C_{1-7}$-alkyl, $C_{2-7}$-alkenyl, $C_{3-7}$-cycloalkyl or $C_{5-8}$-cycloalkenyl, which can be optionally substituted by one or more of the following radicals, the substituents being identical or different: halogen, in particular fluorine, chlorine or bromine, $C_{1-4}$-alkoxy, in particular methoxy or ethoxy, carboxyl, carbalkoxy, in particular methoxycarbonyl or ethoxycarbonyl, phenyl, phenoxy or thiophenyl, it being possible for the phenyl rings to be substituted by halogen or alkyl;

$R^1$ furthermore represents phenyl which can be optionally substituted by one or more of the following radicals, the substituents being identical or different: halogen, in particular chlorine, bromine or fluorine, nitro, amino, OH, CN, $C_{1-4}$-alkyl, in particular methyl, $C_{1-4}$-halogenaolkyl, in particular trifluoromethyl, trichloromethyl or pentafluoroethyl, $C_{1-4}$-alkoxy, methylenedioxy, ethylenedioxy, $C_{1-4}$-halogenoalkoxy, in particular trifluoromethoxy, pentafluoroethoxy, difluoromethylenedioxy or halogen-substituted ethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-4}$-alkylsulphonyl, in particular methylsulphonyl, $C_{1-4}$-halogenoalkylsulphonyl, carboxyl, carbalkoxy, in particular methoxycarbonyl, and the radical $C_{1-4}$—alkoxy—N=CH—, in particular $CH_3$—O—N=CH—, and also represents phenyl, phenoxy, thiophenyl which can be optionally substituted by halogen or $C_{1-4}$-alkyl, and represents carboxyalkoxy having 2–4C atoms, such as carboxymethoxy, $R^1$ furthermore represents heteroaryl, such as pyridinyl, pyrimidinyl, triazinyl, isoxazolyl, thiazolyl, oxadiazolyl, imidazolyl, triazolyl, furanyl or thienyl, which can be optionally one or polysubstituted by identical or different substituents from amongst halogen, in particular chlorine, $C_{1-4}$-alkyl, in particular methyl and ethyl, and $C_{1-4}$-alkoxy, in particular methoxy and ethoxy.

$R^1$ furthermore preferably represents o-, m- or p-chlorophenyl, 2,3-dichlorophenyl, 3,4-dichlorophenyl, 3,5-dichlorophenyl, 2,4-dichlorophenyl, 2,5-dichlorophenyl, 2,6-dichlorophenyl, o-, m- or p-nitrophenyl, o-chloro-methylphenyl, 2,6-dimethoxyphenyl, o-, m- or p-trifluoromethylphenyl, o-, m- or p-methoxyphenyl, o-, m- or p-tolyl, o-, m- or p-trifluoromethoxyphenyl, o-, m- p-fluorophenyl, cyclohexyl, benzyl, butyl, tert.-butyl, fluoro-tert.-butyl, chloro-tert.-butyl, difluoro-tert.-butyl, trichloromethyl, 3-iodophenyl, biphenyl, 4-trimethylsilyloxyphenyl, 4-chloro-3-nitrophenyl, 3-chloro-4-nitrophenyl, 3,4,5-trichlorophenyl, 3,5-dichloro-4-fluorophenyl, 4-difluoromethylphenyl, 3-nitro-4-fluorophenyl, 3-fluoro-4-nitrophenyl, 3-trifluoromethyl-4-chlorophenyl, 4-trifluoromethyl-3-chlorophenyl, 3-chloro-5-trifluoromethylphenyl, 3,4-(di(trifluoromethyl), 3,5-di(trifluoromethyl)phenyl, 3-trifluoromethyl-4,5-dichlorophenyl, 4-trifluoromethyl-3,5-dichlorophenyl, 4-trifluoromethoxy-3nitrophenyl, 4-trifluoromethoxy-3-bromophenyl, 4-nitro-3-trifluoromethoxyphenyl, 4-bromo-3-trifluoromethoxyphenyl, 3-nitro-4-trifluoromethoxy-5-chlorophenyl, 4-methoxy-3,5-dichlorophenyl, 4-methyl-3,5-dichlorophenyl, 4-fluoro-3-bromophenyl, 4-bromo-3-fluorophenyl, 4-chloro-3-methylphenyl, 4-trifluoromethylmercaptophenyl, 4-trifluoromethoxy-3-chlorophenyl, 3-trifluoromethyl-4-chlorophenyl, 4-chlorodifluoromethoxy-3-chlorophenyl, 4-fluoro-3-chlorophenyl, pentafluorophenyl, 4-fluoro-3,5-dibromophenyl, 4-fluoro-3-chloro-5-bromophenyl, 4-chloro-3,5-dibromophenyl, 4-bromo-3,5-dichlorophenyl, 3-bromo-4,5-dichlorophenyl, 3,4,5-trifluorophenyl or 3,4,5-tribromophenyl.

In formula I, $R^2$ preferably represents hydrogen, one equivalent of an alkali metal, of an alkaline earth metal or of an optionally substituted ammonium cation, trialkylsilyl having 1–4C atoms in each alkyl part, $C_{1-4}$-alkyl, $C_{1-4}$-alkylcarbonyl, phenyl or benzoyl, which can be optionally substituted by one or more of the following radicals (A), the substituents being identical or different: (A) represents halogen, in particular chlorine, bromine or fluorine, nitro, amino, CN, $C_{1-4}$-alkyl, in particular methyl, $C_{1-4}$-halogenoalkyl, in particular trifluoromethyl or pentafluoroethyl, $C_{1-4}$-alkoxy, $C_{1-4}$-halogenoalkoxy, in particular trifluoromethoxy or pentafluoroethoxy, methylenedioxy, ethylenedioxy or difluoromethylenedioxy, halogen-substituted ethylenedioxy, such as trifluoroethylenedioxy, $C_{1-4}$-alkylthio, $C_{1-4}$-halogenoalkylthio, in particular trifluoromethylthio, $C_{2-8}$-alkoxyalkyl, $C_{2-8}$-halogenoalkoxyalkyl, $C_{1-5}$-alkylsulphenyl or phenylsulphenyl, which can be optionally substituted, $C_{1-4}$-alkylsulphonyl, in particular methylsulphonyl, $C_{1-4}$-halogenoalkylsulphonyl, carbalkoxy, in particular methoxycarbonyl, and the radical $C_{1-4}$—alkoxy—N=CH—, in particular $CH_3$—O—N=CH—, or phenyl, phenoxy or thiophenyl, which can be optionally substituted by halogen or by $C_{1-4}$-alkyl, and represents carboxyalkoxy having 2–4 C atoms, such as carboxymethoxy;

$R^2$ furthermore represents $C_{1-4}$-alkoxycarbonyl, phenoxycarbonyl which can be optionally substituted by one or more of the radicals (A), $C_{1-4}$-alkylsulphonyl, phenylsulphonyl which can be optionally substituted by one or more of the radicals (A), $C_{1-4}$-alkylaminosulphonyl, $C_{1-5}$-alkylsulphenyl or phenylsulphenyl, which can be optionally substituted, di-$C_{1-4}$-alkylaminosulphonyl, phenylaminosulphonyl which can be optionally substituted by one or more of the radicals (A), phenyl-$C_{1-4}$-alkyl-aminosulphonyl and radicals of the formula

wherein $R^5$ and $R^6$ independently of one another represent hydrogen, $C_{1-20}$-alkyl, $C_{3-6}$-cycloalkyl, phenyl which can be optionally substituted by one or more of the radicals (A), phenylcarbonyl which can be optionally substituted by one or more of the radicals (A), $C_{1-10}$-alkylcarbonyl, $C_{1-4}$-alkylaminocarbonyl, $C_{1-10}$-alkoxycarbonyl, phenylaminocarbonyl or phenylsulphonyl, which can be optionally substituted by one or more of the radicals (A).

In formula I, $R^3$ preferably represents the radicals stated for $R^1$, and CN or the radical —$COR^4$, $R^4$ preferably represents amino, $C_{1-8}$-amino, $C_{1-8}$-alkylamino or di-$C_{1-8}$-alkylamino, which can be optionally substituted by hydroxyl or $C_{1-4}$-alkoxy, phenylamino which can be optionally substituted by one or more of the radicals (A) given above, $C_{5-6}$-cycloalkylamino, a saturated heterocyclic structure having 5–6 C atoms in the ring, such as morpholine or tri-$C_{1-4}$-alkylsilylamino, and radicals of the formula —$NHR^7$ wherein $R^7$ represents $C_{1-4}$-alkylcarbonyl, such as acetyl, $C_{2-4}$-alkenylcarbonyl, $C_{5-8}$-cycloalkenylcarbonyl, $C_{1-4}$-alkylamino, such as methylamino or t-butylamino, phenylamino which can be optionally substituted by one or more of the radicals (A) given above, $C_{1-4}$-alkylaminocarbonylamino

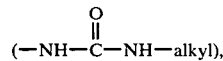

phenylaminocarbonylamino

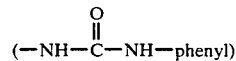

which can be optionally substituted by one or more of the radicals (A), $C_{1-4}$-alkylcarbonylamino

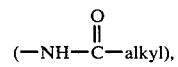

or benzoylamino which can be optionally substituted by one or more of the radicals (A), $R^4$ furthermore represents a radical of the formula

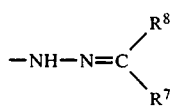

wherein $R^8$ represents $C_{1-4}$-alkyl, in particular methyl, or phenyl which can be optionally substituted by one or more of the radicals (A), $R^9$ represents hydrogen or $C_{1-4}$-alkyl.

In formula I,

Y preferably represents O and

X preferably represents SO and $>SiR^{10}R^{11}$, wherein $R^{10}$ and $R^{11}$ represents $C_{1-4}$-alkyl, in particular methyl.

Particularly preferred compounds of the formula I are those
in which $R^1$ represents $C_{1-6}$-alkyl which is optionally substituted by halogen, in particular chlorine, or by $C_{1-4}$-alkoxycarbonyl, in particular ethoxycarbonyl, or by phenoxy, the phenoxy radical being optionally substituted by halogen, such as chlorine or fluorine, or by methyl, $C_{5-6}$-cycloalkyl, optionally carboxyl-substituted $C_{2-4}$-alkenyl, or phenyl which is optionally substituted by halogen, in particular fluorine or chlorine, $C_{1-4}$-alkyl, in particular methyl, $C_{1-4}$-alkoxy, $C_{1-4}$-halogenoalkoxy, $C_{1-4}$-halogenoalkyl, $NH_2$, $CH_3O$—N=CH— or nitro, and $R^2$ represents hydrogen, $C_{1-6}$-alkyl, $C_{2-4}$-alkenyl, $C_{2-4}$-alkinyl, one equivalent of a cation from the series comprising sodium, potassium, calcium, ammonium, tri-($C_{1-4}$-alkyl)-ammonium and morpholinyl, or represents $C_{1-4}$-alkylsulphenyl, $C_{1-4}$-halogenoalkylsulphenyl, phenylsulphenyl which is optionally substituted by halogen or $C_{1-4}$-alkyl, or phenyl which is optionally substituted by halogen or $C_{1-4}$-alkyl, and $R^3$ represents the radicals stated for $R^1$, and the radical $COR^4$, wherein $R^4$ preferably represents amino, $C_{1-4}$-alkylamino or $C_{1-4}$-alkoxy, X represents SO or $>Si(CH_3)_2$ and Y represents O.

Compounds which should be very particularly mentioned are those of the general formula I
in which $R^1$ represents $C_{1-4}$-alkyl, in particular methyl or t-butyl, methylcarbonyl-$C_{1-4}$-alkoxy, such as methylcarbonylethoxy, $C_{1-4}$-halogenoalkyl, in particular chloromethyl, phenoxymethyl which is optionally substituted by chlorine, fluorine or methyl, or phenyl which is optionally one to trisubstituted by identical or different substituents from amongst halogen, in particular fluorine, chlorine, bromine and iodine, $C_{1-4}$-alkyl, in particular methyl, nitro and $C_{1-4}$-alkoxy, $R^2$ represents hydrogen, sodium, $C_{1-4}$-alkyl, in particular methyl or ethyl, $C_{1-4}$-halogenoalkyl, optionally halogen-substituted $C_{1-4}$-alkylsulphenyl, in particular chlorofluoromethylsulphenyl, $C_{1-4}$-alkylcarbonyl, in particular methylcarbonyl, optionally halogen-substituted phenyl, phenylcarbonyl or phenylsulphenyl, $C_{1-4}$-alkenyl, in particular allyl, $C_{1-4}$-alkinyl, in particular propargyl, trialkylsilyl, in particular trimethylsilyl, and $$-\overset{\overset{\displaystyle O}{\|}}{C}-NR^5R^6,$$

wherein $R^5$ represents hydrogen and $R^6$ represents optionally halogen-substituted phenyl or phenylcarbonyl or represents $C_{1-4}$-alkyl or $C_{1-4}$-alkylcarbonyl, $R^3$ represents the radicals stated for $R^1$, and the radical $COR^4$, wherein $R^4$ represents amino, X represents SO and $Si(CH_3)_2$, and Y represents O.

Compounds which may be particularly mentioned are those of the formula I
in which $R^1$ represents t-butyl, chloromethyl, $C_{1-4}$-alkoxycarbonylmethyl, phenoxymethyl which is optionally substituted by chlorine or fluorine, and phenyl which is optionally mono- or polysubstituted by chlorine, methyl, nitro or trifluoromethyl, and $R^2$ represents hydrogen, sodium, methyl, ethyl, phenyl, 3,4-dichlorophenyl, propargyl, trihalogenomethylsulphenyl, tri($C_{1-4}$-alkyl)ammonium or morpholinyl, and $R^3$ represents the radicals stated for $R^1$ and represents $COR^4$, wherein $R^4$ represents amino.

The following compounds of the formula I may be mentioned individually:

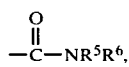

| $R^1$ | $R^2$ | $R^3$ | X |
|---|---|---|---|
| C₆H₅– | H | CONH₂ | SO |
| C₆H₅– | CH₃ | CONH₂ | SO |
| C₆H₅– | H₂C=CH—CH₂— | CONH₂ | SO |
| C₆H₅– | CH₃CO— | CONH₂ | SO |
| C₆H₅– | CH₃—NH—CO— | CONH₂ | SO |
| C₆H₅– | H | CCl₃ | SO |
| C₆H₅– | H | —CH₂COOC₂H₅ | SO |
| 4-Cl-C₆H₄– | H | CONH₂ | SO |
| 4-Cl-C₆H₄– | Na⁺ | CONH₂ | SO |

-continued $$\begin{array}{c} \text{O}= \\ \text{R}^2-\text{N}-\text{X}-\text{O} \end{array} \begin{array}{c} \text{R}^1 \\ \text{R}^3 \end{array}$$

| R¹ | R² | R³ | X |
|---|---|---|---|
| 4-Cl-C₆H₄– | CH₃ | CONH₂ | SO |
| 4-Cl-C₆H₄– | C₂H₅ | CONH₂ | SO |
| 4-Cl-C₆H₄– | 4-Cl-C₆H₄-CH₂– | CONH₂ | SO |
| 4-Cl-C₆H₄– | CH₃SO₂– | CONH₂ | SO |
| 3,4-Cl₂-C₆H₃– | H | CONH₂ | SO |
| 3,4-Cl₂-C₆H₃– | Na⁺ | CONH₂ | SO |
| 3,4-Cl₂-C₆H₃– | (C₂H₅)₃NH⁺ | CONH₂ | SO |
| 3,4-Cl₂-C₆H₃– | CH₃ | CONH₂ | SO |
| 3,4-Cl₂-C₆H₃– | C₂H₅ | CONH₂ | SO |
| 3,4-Cl₂-C₆H₃– | n-C₃H₇ | CONH₂ | SO |

-continued $$\underset{R^2}{\overset{O}{\|}}\underset{X}{N}\underset{O}{\overset{R^1}{\underset{R^3}{|}}}$$

| R¹ | R² | R³ | X |
|---|---|---|---|
| 3,4-diClC₆H₃- | H₂C=CH-CH₂- | CONH₂ | SO |
| 3,4-diClC₆H₃- | HC≡C-CH₂- | CONH₂ | SO |
| 3,4-diClC₆H₃- | CH₃CO- | CONH₂ | SO |
| 3,4-diClC₆H₃- | CH₃NH-CO- | CONH₂ | SO |
| 3,4-diClC₆H₃- | CCl₃S- | CONH₂ | SO |
| 3,4-diClC₆H₃- | CFCl₂S- | CONH₂ | SO |
| 3,4-diClC₆H₃- | 4-ClC₆H₄-S- | CONH₂ | SO |
| 3,4-diClC₆H₃- | 3,4-diClC₆H₃-NH-CO- | CONH₂ | SO |
| 3,4-diClC₆H₃- | 4-CH₃-C₆H₄-SO₂- | CONH₂ | SO |

-continued
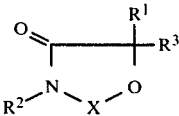
| R¹ | R² | R³ | X |
|---|---|---|---|
| 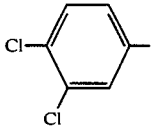 | 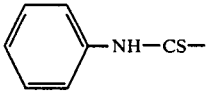 | CONH₂ | SO |
| 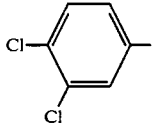 | 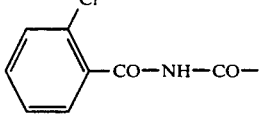 | CONH₂ | SO |
| 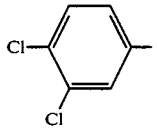 | 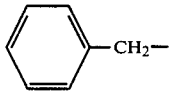 | CONH₂ | SO |
| 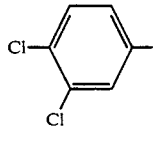 | 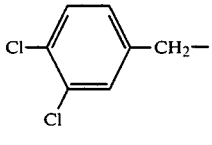 | CONH₂ | SO |
| 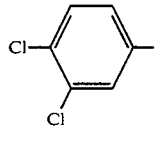 | n-C₄H₉—NH—CO— | CONH₂ | SO |
| 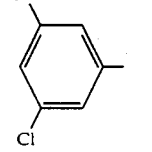 | H | CONH₂ | SO |
| 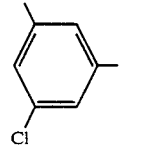 | Na⁺ | CONH₂ | SO |
| 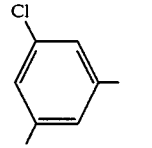 | CH₃ | CONH₂ | SO |
| 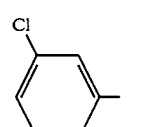 | HC≡C—CH₂— | CONH₂ | SO |

-continued $$\begin{array}{c} O \quad R^1 \\ \parallel \quad | \\ C-R^3 \\ | \quad | \\ R^2-N\phantom{-}O \\ \phantom{R^2-N}X \end{array}$$

| R¹ | R² | R³ | X |
|---|---|---|---|
| 3,5-dichlorophenyl | (CH₃)₂CH— | CONH₂ | SO |
| 2,4-dichlorophenyl | CCl₃S— | CONH₂ | SO |
| 3,5-dichlorophenyl | cyclohexyl | CONH₂ | SO |
| 3,5-dichlorophenyl | n-C₁₂H₂₅ | CONH₂ | SO |
| 3,4,5-trichlorophenyl | H | CONH₂ | SO |
| 3,5-dichloro-4-fluorophenyl | H | CONH₂ | SO |
| 4-(CF₃)phenyl | H | CONH₂ | SO |
| 4-(CF₃)phenyl | CH₃ | CONH₂ | SO |
| 2-chloro-5-nitrophenyl | H | CONH₂ | SO |

-continued
$$\underset{R^2}{\overset{O}{\underset{\|}{\text{N}}}}\underset{X}{\overset{R^1}{\underset{|}{\text{C}}}}\underset{O}{\overset{R^3}{\underset{|}{\text{}}}}$$
| R¹ | R² | R³ | X |
|---|---|---|---|
| 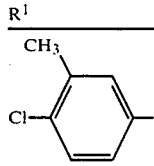 2-CH₃, 4-Cl-phenyl | H | CONH₂ | SO |
| 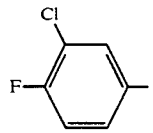 3-Cl, 4-F-phenyl | H | CONH₂ | SO |
| 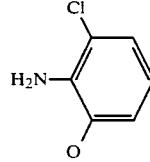 3-Cl, 4-NH₂, 5-O-phenyl | H | CONH₂ | SO |
| 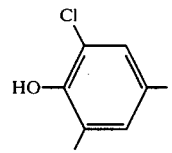 3,5-diCl, 4-OH-phenyl | H | CONH₂ | SO |
| 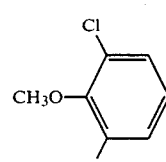 3,5-diCl, 4-OCH₃-phenyl | H | CONH₂ | SO |
| 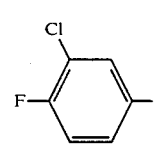 3-Cl, 4-F-phenyl | CH₃ | CONH₂ | SO |
| 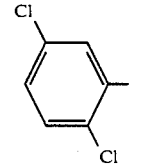 2,5-diCl-phenyl | H | CONH₂ | SO |
| 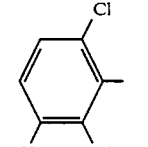 2,3,4-triCl-phenyl | H | CONH₂ | SO |
| 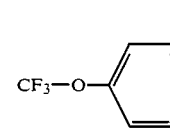 4-(CF₃O)-phenyl | H | CONH₂ | SO |

-continued
$$\begin{array}{c} O=\overset{R^1}{\underset{R^2-N-X-O}{|}}R^3 \end{array}$$
| R¹ | R² | R³ | X |
|---|---|---|---|
| 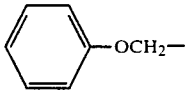 C₆H₅-O-CH₂- | H | CONH₂ | SO |
| 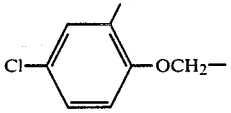 2,4-Cl₂C₆H₃-O-CH₂- | H | CONH₂ | SO |
| ClCH₂ | H | t-C₄H₉ | SO |
| BrCH₂ | H | 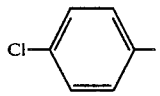 4-Cl-C₆H₄- | SO |
| 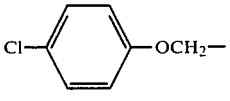 4-Cl-C₆H₄-O-CH₂- | H | t-C₄H₉ | SO |
| 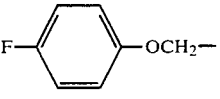 4-F-C₆H₄-O-CH₂- | H | t-C₄H₉ | SO |
| 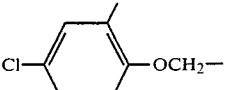 2,4-Cl₂C₆H₃-O-CH₂- | H | t-C₄H₉ | SO |
| 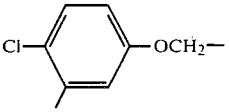 3,4-Cl₂C₆H₃-O-CH₂- | H | t-C₄H₉ | SO |
| 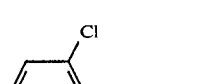 2,6-Cl₂C₆H₃-O-CH₂- | H | t-C₄H₉ | SO |
| 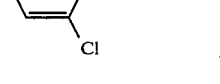 2-Cl-4-F-C₆H₃-O-CH₂- | H | t-C₄H₉ | SO |
| 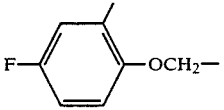 2-Br-4-F-C₆H₃-O-CH₂- | H | t-C₄H₉ | SO |

-continued $$\underset{R^2}{\overset{O}{\underset{\|}{C}}}\underset{X}{\overset{R^1}{\underset{|}{C}}}\underset{O}{\overset{R^3}{|}}$$

| R¹ | R² | R³ | X |
|---|---|---|---|
| C₆H₅-SO₂CH₂- | H | t-C₄H₉ | SO |
| 4-Cl-C₆H₄-OCH₂- | CH₃ | t-C₄H₉ | SO |
| 4-Cl-C₆H₄-OCH₂- | C₂H₅ | t-C₄H₉ | SO |
| C₆H₅- | H | -CON(morpholino) | SO |
| 4-Cl-C₆H₄- | H | CONH₂ | Si(CH₃)₂ |
| 3,4-Cl₂-C₆H₃- | H | CONH₂ | Si(CH₃)₂ |
| 3,5-Cl₂-C₆H₃- | H | CONH₂ | Si(CH₃)₂ |
| C₆H₅- | H | CONH₂ | Si(CH₃)₂ |
| 3,4,5-Cl₃-C₆H₂- | H | CONH₂ | Si(CH₃)₂ |
| 3,5-Cl₂-4-F-C₆H₂- | H | CONH₂ | Si(CH₃)₂ |

-continued

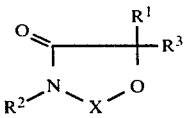

| R¹ | R² | R³ | X |
|---|---|---|---|
| 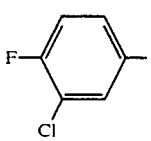 (3-Cl, 4-F phenyl) | H | CONH₂ |  Si(CH₃)₂ |
| 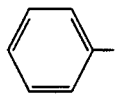 (phenyl) | C₂H₅ | COOCH₃ | $-\overset{\overset{O}{\|}}{P}-OC_2H_5$ |
| 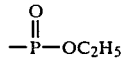 (3,4-Cl₂ phenyl) | C₂H₅ | CONH₂ | $-\overset{\overset{O}{\|}}{P}-OC_2H_5$ |
| 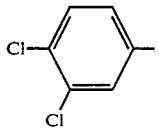 (4-Cl phenyl) | C₂H₅ | CONH₂ | $-\overset{\overset{O}{\|}}{P}-OC_2H_5$ |
| 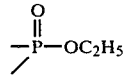 (phenyl) | C₂H₅ | CONH₂ | $-\overset{\overset{O}{\|}}{P}-OC_2H_5$ |
| 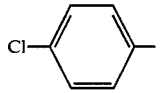 (3,4-Cl₂ phenyl) | H | CONH₂ | S |
| 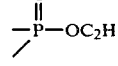 (3,4-Cl₂ phenyl) | H | CONH₂ | SO₂ |
| 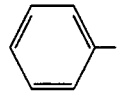 (4-Cl-phenoxymethyl) | H | tC₄H₉ | SO₂ |

The following compounds may also be mentioned:

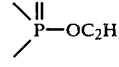

| R¹ | R² | R³ |
|---|---|---|
| t-Butyl | H | 3,4-Cl₂—C₆H₃OCH₂— |
| t-Butyl | CH₃ | " |
| t-Butyl | C₂H₅ | 3,4-Cl₂—C₆H₃OCH₂— |
| t-Butyl | C₃H₇ | " |

-continued

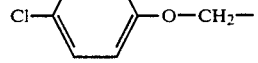

| R¹ | R² | R³ |
|---|---|---|
| t-Butyl | n-C₄H₉ | " |
| t-Butyl | i-C₃H₇ | " |
| t-Butyl | HC≡C—CH₂— | " |
| t-Butyl | H₂C=CH—CH₂— | " |

-continued $$\underset{R^2}{\overset{O}{\underset{\|}{\text{N}}}}\overset{R^1}{\underset{\|}{\text{C}}}\overset{R^3}{\underset{O}{\text{O}}}$$

(Structure: 5-membered ring with N-R², C=O, C(R¹)(R³), O, S(=O)₂)

| R¹ | R² | R³ |
|---|---|---|
| t-Butyl | C₆H₅—CH₂— | " |
| t-Butyl | Cl—C₆H₄—CH₂— | " |
| t-Butyl | 3,4-Cl₂—C₆H₃—CH₂— | " |
| t-Butyl | C₆H₅—CH₂— | 4-Cl—C₆H₄OCH₂— |
| t-Butyl | Cl—C₆H₄—CH₂— | " |
| t-Butyl | i-C₃H₇ | " |
| t-Butyl | n-C₄H₉ | " |
| t-Butyl | n-C₈H₁₇ | " |
| t-Butyl | 3,4-Cl₂—C₆H₃—CH₂— | " |
| 4-Cl—C₆H₄— | H | 4-Cl—C₆H₄OCH₂— |
| " | CH₃ | " |
| " | C₂H₅ | " |
| " | n-C₃H₇ | " |
| " | i-C₃H₇ | " |
| " | HC≡C—CH₂— | " |
| " | H₂C=CH—CH₂— | " |
| " | n-C₄H₉ | " |
| " | Cl—C₆H₄—CH₂— | " |
| " | 3,4-Cl₂—C₆H₃—CH₂— | " |
| " | H | 3,4-Cl₂—C₆H₃OCH₂— |
| " | CH₃ | " |
| " | C₂H₅ | " |
| " | C₃H₇ | " |
| " | i-C₃H₇ | " |
| " | n-C₄H₉ | " |
| " | H₂C=CH—CH₂ | " |
| " | HC≡C—CH₂ | " |
| " | C₆H₅—CH₂ | " |
| 3,4-Cl₂—C₆H₃ | H | 4-Cl—C₆H₄OCH₂— |
| " | CH₃ | " |
| " | C₂H₅ | " |
| 3,4-Cl₂—C₆H₃— | n-C₃H₇ | 4-Cl—C₆H₄OCH₂— |
| " | i-C₃H₇ | " |
| " | HC≡C—CH₂— | " |
| " | H₂C=CH—CH₂— | " |

-continued

| R¹ | R² | R³ |
|---|---|---|
| " | Cl—C₆H₄—CH₂— | " |
| " | 3,4-Cl₂—C₆H₃—CH₂— | " |
| " | H | 3,4-Cl₂—C₆H₃OCH₂— |
| " | CH₃ | " |
| " | C₂H₅ | " |
| " | C₃H₇ | " |
| " | i-C₃H₇ | " |
| " | HC≡C—CH₂— | " |
| " | H₂C=CH—CH₂— | " |
| " | n-C₄H₉ | " |
| " | C₆H₅—CH₂— | " |
| " | n-C₆H₁₃ | " |
| 4-Cl—C₆H₄— | CH₃ | CONH₂ |
| " | C₂H₅ | " |
| " | HC≡C—CH₂— | " |
| " | H₂C=CH—CH₂— | " |

Process 2a

The reaction of the compounds of the formulae II and III is carried out, if required, in the presence of catalysts. It is carried out, if appropriate, in the presence of diluents. It can be described, for example, by the following equations:

(Reaction scheme: C₆H₅-C(NH₂)(OH)-CONH₂ + SOCl₂ → cyclic sulfamidate with C₆H₅, CONH₂ substituents)

-continued

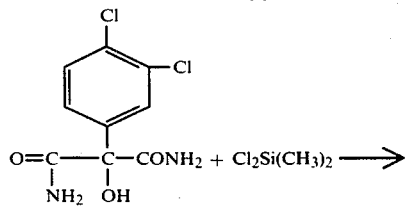

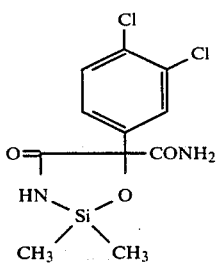

Compounds of the formula II have been disclosed, for example in DE-OS (German Published Specification) No. 3,140,275, and compounds of the formula II can be prepared by known methods.

Some of the compounds of the formula II form the subject of Application Ser. No. 546,687, filed Oct. 28, 1983, now pending, (German Application Pat. No. 33 08462.9). They can be prepared by the processes stated therein.

The following compounds of the formula II may be mentioned individually: Hydroxymalonic acid diamides, such as phenyl-hydroxy-malonic acid diamide, 2-, 3- and 4-chlorophenylhydroxy-malonic acid diamide, 2,3-dichlorophenyl-hydroxy-malonic acid diamide, 3,4-dichlorphenyl-hydroxy-malonic acid diamide, 4-methoxy-3,5-dichloro-phenyl-hydroxy-malonic acid diamide, 4-amino-3,5-dichloro-phenyl-hydroxy-malonic acid diamide, 4-hydroxy-3,5-dichloro-phenyl-hydroxy-malonic acid diamide, 3,5-dichloro-phenyl-hydroxy malonic acid diamide, 2,4-dichloro-phenyl-hydroxy-malonic acid diamide, 2,5-dichloro-phenyl-hydroxy-malonic acid diamide, 2,6-dichloro-phenyl-hydroxy-malonic acid diamide, 2-, 3- and 4-nitrophenyl-hydroxy-malonic acid diamide, 2-chloro-methylphenyl-hydroxy-malonic acid diamide, 2-, 3- and 4-trifluoromethylphenyl-hydroxy-malonic acid diamide, 2-, 3- and 4-methoxyphenyl-hydroxy-malonic acid diamide, 2,6-dimethoxyphenyl-hydroxy-malonic acid diamide, 2-, 3- and 4-tolyl-hydroxy-malonic acid diamide, 2-, 3- and 4-trifluoromethoxyphenyl-hydroxy-malonic acid diamide, 2-, 3- and 4-fluorophenyl-hydroxymalonic acid diamide, 3,4-dichlorophenyl-hydroxy-malonic acid amide methylamide, phenyl-hydroxy-malonic acid diethylamide amide, cyclohexylhydroxy-malonic acid methyl ester amide, dimethyl 3,4-dichlorophenyl-hydroxy-malonate, diethyl 3-chlorophenyl-hydroxy-malonate, 3,4,5-trichlorophenylhydroxy-malonic acid methyl ester amide, 4-chlorophenylhydroxy-malonic acid isopropyl ester amide, 3,5-dichlorophenyl-hydroxy-malonic acid amide morpholinylamide, 3,4-dichlorophenyl-hydroxy-malonic acid bis-isopentylamide, phenylhydroxy-malonic acid bismethylamide, cyclohexylhydroxy-malonic acid diamide, 2,3,4-; 2,3,6- and 3,4,5-trichlorophenyl-hydroxy-malonic acid diamide, 2,3,4,5-and 2,3,5,6-tetrachlorophenyl-hydroxy-malonic acid diamide and pentachlorophenyl-hydroxy-malonic acid diamide.

α,α'-disubstituted hydroxyacetic acid amides, such as α-trichloromethyl-α'-phenyl-, α-t-butyl-α'-4-chlorophenoxy-methyl-, α-t-butyl-α'-2,4-dichlorophenoxymethyl-, α-t-butyl-α'-4-fluorophenoxymethyl-, α-t-butyl-α'-2,6-di-chlorophenoxymethyl-, α-t-butyl-α'-phenylsulphonylmethyl-, α-t-butyl-α'-chloromethyl-, α-t-butyl-α'-3,4-dichlorophenoxymethyl-, α-phenyl-α'-ethoxycarbonylmethyl-, α-t-butyl-α'-4-fluoro-2-chlorophenoxymethyl-, α-t-butyl-α'-4-fluoro-2-bromophenoxymethyl- and α-t-butyl-60 '-phenoxymethyl-hydroxyacetic acid amide.

The compounds of the formula III are known. The following may be mentiond: thionyl chloride, sulphur dichloride and di($C_{1-4}$-alkyl)-silyl dichloride.

The reaction is particularly preferably carried out using thionyl chloride.

If thionyl chloride is employed as the compound of the formula III, the reaction with the compounds of the formula II is preferably carried out in a large excess of thionyl chloride, without the use of diluents. The compounds of the formula II are either added to the initially introduced amount of thionyl chloride, or the thionyl chloride is added to the compound of the formula II. In this procedure, thionyl chloride serves as the reactant and as the diluent. The reaction is carried out under reflux at an elevated temperature in the range of 50°–150° C., preferably 60°–100° C., particularly preferably at the boiling point of the mixture.

The reaction is preferably carried out under atmospheric pressure. It is possible to carry out the reaction under elevated pressure.

Working up is carried out by distilling off the thionyl chloride, rinsing the residue, for example with the ether, and drying the residue.

Under certain circumstances, the compound of the formula I can also be filtered off directly from the excess thionyl chloride, washed and dried.

The reaction of the compounds of the formula II with thionyl chloride or sulphur dichloride or dialkylsilyl dichloride can be carried out in the presence of the diluent.

Preferably used diluents are optionally chlorinated hydrocarbons, such as benzene, toluene, xylene, cyclohexane, petroleum ether, methylene chloride, chloroform, carbon tetrachloride, chlorobenzene, ethers, such as diethyl ether, dimethyl ether, dioxane and tetrahydrofuran, and esters, such as ethyl acetate.

The compounds of the formula II are dissolved or suspended in the diluent, and thionyl chloride, or sulphur dichloride or dialkylsilyl dichloride is added.

The compounds of the formula II and III can be employed in an equimolar ratio. However, a 1-fold to 2-fold excess of the compound of the formula III, such as, for example, thionyl chloride, is preferred.

The reaction is carried out at temperatures of 40°–150° C., preferably at 40°–100° C. The reaction is particularly advantageously carried out under reflux at the boiling point of the mixture.

The reaction is carried out under atmospheric pressure. However, it can also be carried out under elevated pressure. After thionyl chloride or sulphur dichloride or dialkylsilyl dichloride and the diluent have been distilled off, working up is carried out as described above, for example by recrystallisation and drying of the residue.

The compounds of the formula I in which R² represents hydrogen, which are obtainable by process 2a, can, if required, be converted to their salts by treating them with an equimolar amount of a base. Suitable bases are alkali metal hydroxides or alkaline earth metal hydroxides, such as NaOH, Ca(OH)₂ or KOH, alkali metal alcoholates or alkaline earth metal alcoholates, such as sodium methylate or ethylate, and tertiary amines, such as trimethylamine, triethylamine, pyridine or morpholine.

Process 2b

The reaction of the compounds of the formula IV with compounds of the formula V is carried out, if appropriate, in the presence of diluents and catalysts. It can be described, for example, by the following equation:

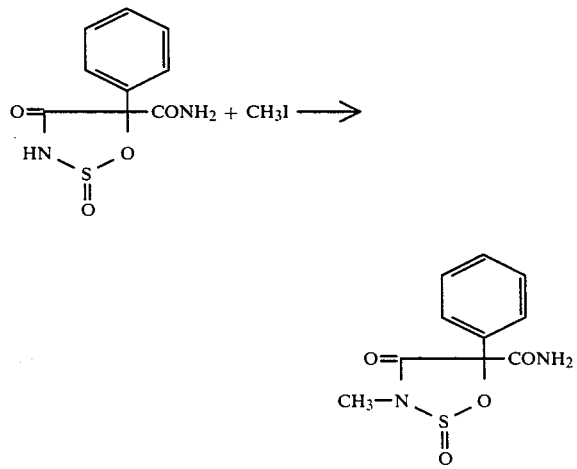

The compounds of the formula IV are obtainable by the process described above for the preparation of the compounds of the formula I. The compounds of the formula I in which R³ represents hydrogen, which are mentioned above as being preferred, are preferably employed.

The compounds of the formula V are known. The following may be mentioned as examples of compounds of the formula (V): alkylating agents, such as methyl bromide, methyl iodide, methyl chloride, ethyl bromide, ethyl chloride, ethyl iodide, 1-iodopropane, 2-iodopropane, allyl chloride, allyl bromide, propargyl bromide, propargyl chloride, benzyl chloride, benzyl bromide, 3,4-dichlorobenzyl chloride, dimethyl sulphate and diethyl sulphate.

Acylating agents, such as benzoyl chloride, 3,4-dichlorobenzoyl chloride, 3-chlorobenzoyl bromide, acetyl chloride, acetic anhydride, propionyl chloride, benzoyl cyanide, ethyl chloroformate, methyl chloroformate, methylsulphamoyl chloride, dimethylcarbamoyl chloride and phenyl chloroformate.

Isocyanates, such as methyl isocyanate, ethyl isocyanate, propyl isocyanate, butyl isocyanate, dodecyl isocyanate, phenyl isocyanate, p-chlorobenzoyl (isocyanate, o-chlorobenzoyl isocyanate, sulphonyl isocyanates, such as benzenesulphonyl isocyanate, and 3,4-dichlorobenzoyl isocyanate.

Sulphenylating agents, such as trihalogenomethylsulphenyl chloride, 2,3-trichloromethyl-, dichlorofluoromethyl- and trifluoromethylsulphenyl chloride, optionally substituted phenylsulphenyl chloride, such as, for example, phenyl-, p-chlorophenyl-, p-trifluoromethylphenyl- and 3,4-dichlorophenylsulphenyl chloride. Silylating agents, such as, for example, trimethylsilyl cyanide or chloride. Sulphonylating agents, such as, for example, tosyl chloride, phenylsulphonyl chloride and chlorophenylsulphonyl chloride.

Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, as well as ethers, such as diethyl ether and dibutyl ether, glycol dimethyl ether and diglycol dimethyl ether, tetrahydrofuran and dioxane, and furthermore ketones, such as acetone, methyl ethyl ketone, methyl isopropyl ketone and methyl isobutyl ketone, and in addition esters, such as methyl acetate and ethyl acetate, and nitriles, such as, for example, acetonitrile and propionitrile, benzonitrile and glutarodinitrile, and furthermore amides, such as, for example, dimethylformamide, dimethylacetamide and N-methylpyrrolidone, as well as dimethylsulphoxide, tetramethylenesulphone and hexamethylphosphoric acid triamide.

All customary acid-binding agents can be used as acid acceptors. These preferably include alkali metal carbonates, hydroxides or alcoholates, such as sodium carbonate, potassium carbonate, sodium hydroxide, potassium hydroxide, sodium methylate, potassium methylate, sodium ethylate and potassium ethylate, and also aliphatic, aromatic or heterocyclic amines, for example trimethylamine, triethylamine, tributylamine, dimethylaniline, dimethylbenzylamine and pyridine.

Suitable catalysts are compounds which are usually used, in reactions in two-phase systems comprising water and water-immiscible organic solvents, for phase-transfer of reactants (phase-transfer catalysts). Particularly preferred catalysts of this type are tetraalkyl- and trialkylaralkyl-ammonium salts having preferably 1 to 10, in particular 1 to 8, carbon atoms per alkyl group, preferably phenyl as the aryl constituent of the aralkyl group and preferably 1 to 4, in particular 1 or 2, carbon atoms in the alkyl part of the aralkyl group. Particularly suitable compounds of this type are the halides, such as chlorides, bromides and iodides, preferably the chlorides and bromides. Tetrabutylammonium bromide, benzyl-triethylammonium chloride and methyl trioctylammonium chloride may be mentioned as examples.

The reaction temperature is kept between about 0° C. and 130° C., preferably between about 20° C. and 60° C. The process is preferably carried out under atmospheric pressure.

Working up is effected in a customary manner. Process 2c:

The reaction of the compounds of the formula II with silyl dicyanides of the formula IX is carried out as described for process 2a (varient using diluents).

The process is preferably carried out in the presence of catalytic (0.01–5% by weight) to equimolar amounts of a base. tert.-Amines, such as trimethylamine, triethylamine or pyridine, may be preferably mentioned as bases.

Process 2d

The reaction of the compounds of the formula X with compounds of the formula XI can be represented by the following equation:

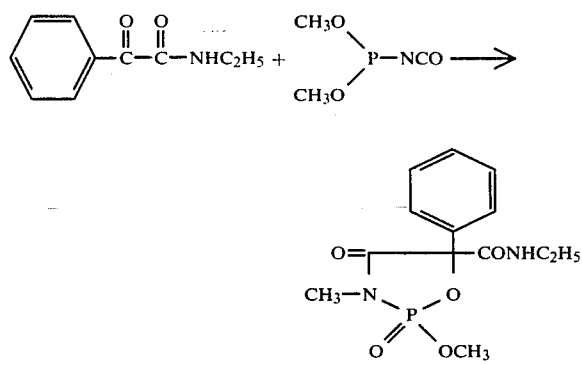

Compounds of the formula X are known and can be prepared analogously to known processes.

Compounds of the formula XI are known and can be prepared analogously to known processes (see Journ. Gen. Chem. USSR Volume 38 III (1968) pages 1479–1482).

The reaction is carried out in a diluent which is inert towards the educts. Suitable diluents of this type are those mentioned for process 2a.

The compounds of the formulae X and XI are preferably employed in an equimolar amount.

The reaction is carried out at temperatures from $-20°$ C. to $+50°$ C., preferably $-10°$ C. to $+20°$ C.

The educts are mixed and stirred until the reaction is complete. The end of the reaction can be determined spectroscopically, and is indicated by the vanishing of the NCO band in the reaction mixture.

Working up is effected by distilling off the diluent in a conventional manner.

As already mentioned, the preparation of the compounds of the formula II forms the subject of Application Ser. No. 546,687 (German Application Pat. No. 33 08462.9).

Their preparation is described below, in a general form:

3. Compounds of the formula XII

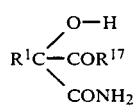     XII in which
$R^1$ has the meaning given under 1 and
$R^{17}$ represents amino, optionally substituted alkoxy or cycloalkoxy, alkylamino, arylamino, dialkylamino, cycloalkylamino, alkenylamino or nitrogen-containing saturated heterocyclic radicals with optionally contain further heteroatoms, it being possible for the radicals to be optionally substituted,
are obtained by a process in which compounds of the formula XIII

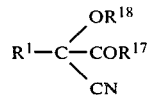     XIII in which
$R^1$ has the meaning given under 1,
$R^{18}$ represents hydrogen or $Si(CH_3)_3$ and
$R^{17}$ has the meaning given above,
are reacted with inorganic acids.

4. Compounds of the formula XIV

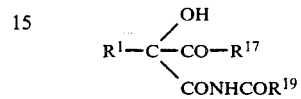     XIV in which
$R^1$ has the meaning given under 1,
$R^{17}$ has the meaning given under 3 and
$R^{19}$ represents hydrogen, optionally substituted alkyl, alkenyl, cycloalkenyl or aryl,
are obtained by a process in which compounds of the formula XV

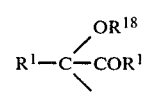     XV in which
$R^1$ and $R^{17}$ have the meaning given above and
$R^{18}$ represents hydrogen or $Si(CH_3)_3$, are reacted with acids of the formula XVI

     XVI in which
$R^{19}$ has the meaning given above,
in the presence of inorganic acids.

5. Compounds of the formula XVII

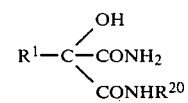     XVII in which
$R^1$ has the meaning given under 1 and
$R^{20}$ represents alkyl, cycloalkyl, alkenyl, amino, alkylamino, arylamino, acylamino, dialkylamino or alkylarylamino, are obtained by a process in which compounds of the formula XVIII

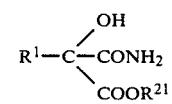     XVIII in which
$R^1$ has the meaning given above and
$R^{21}$ represents alkyl or cycloalkyl,
are reacted with compounds of the formula XIX

     XIX in which
R$^{20}$ has the meaning given above.

6. Compounds of the formula XX

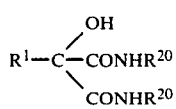  XX in which
R$^1$ and R$^{20}$ have the meaning given under 5, are obtained by a process in which compounds of the formula XXI

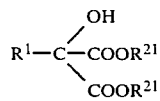  XXI in which
R$^1$ has the meaning given above and
R$^{21}$ are identical or different and represent alkyl or cycloalkyl,
are reacted with compounds of the formula XIX

  XIX in which
R$^{20}$ has the meaning given above.

7. Compounds of the formula XXII

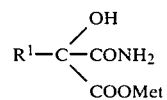  XXII in which
R$^1$ has the meaning given under 1, and
Met represents one equivalent of an alkali metal cation or alkaline earth metal cation,
are obtained by a process in which compounds of the formula XVIII

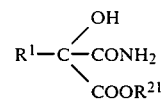  XVIII in which
R$^1$ and R$^{21}$ have the meaning given under 5. are reacted with compounds of the formula XXIII

  XXIII in which
Met has the meaning given above.

8. Compounds of the formula XXIV

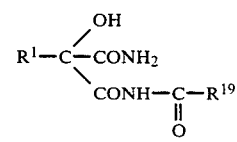  XXIV in which
R$^1$ has the meaning given under 1 and
R$^{19}$ has the meaning given under 4, are obtained by a process in which compounds of the formula XXV

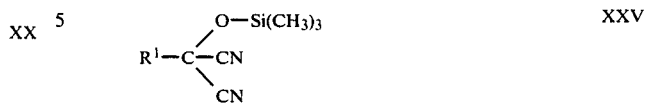  XXV in which
R$^1$ has the meaning given above, are reacted with acids of the formula XVI

  XVI in which
R$^{19}$ has the meaning given above, or with their anhydrides in the presence of inorganic mineral acids.

9. Compounds of the formula XXVI

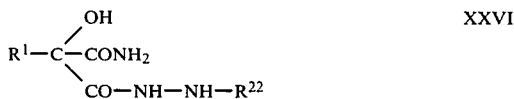  XXVI in which
R$^1$ has the meaning given under 1 and
R$^{22}$ represents alkylaminocarbonyl, alkylaminothiocarbonyl, arylaminocarbonyl, arylaminothiocarbonyl, alkylsulphonylaminocarbonyl, arylsulphonylaminocarbonyl, alkylcarbonylaminocarbonyl, arylcarbonylaminocarbonyl and the corresponding thiocarbonyls,
are obtained by a process in which compounds of the formula XXVII

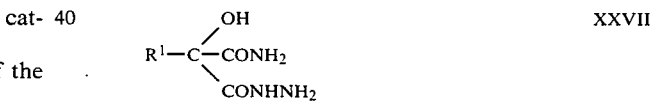  XXVII in which
R$^1$ has the meaning given above, are reacted with iso-(thio)-cyanates of the formula XXVIII

  XXVIII in which
R$^{23}$ represents alkyl, aryl, alkylsulphonyl, arylsulphonyl, alkylcarbonyl or arylcarbonyl.

10. Compounds of the formula XXIX

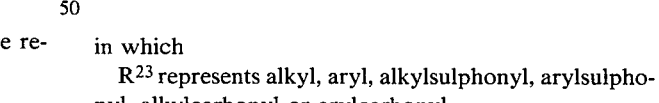  XXIX in which
R$^1$ has the meaning given under 1 and
R$^{24}$ represents alkylcarbonyl, arylcarbonyl, alkylsulphonyl or arylsulphonyl,
are obtained by a process in which compounds of the formula XXVII

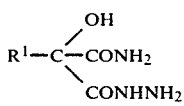 XXVII in which
R[1] has the meaning given above, are reacted with acylating agents of the formula XXX

R[24]—A  XXX in which
R[24] has the meaning given above and
A represents halogen, CN, $C_{1-4}$-alkylcarbonyloxy or arylcarbonyloxy.

11. Compounds of the formula XXXI

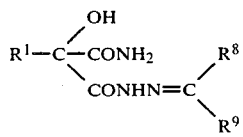 XXXI in which
R[1], R[8] and R[9] have the meaning given under 1, are obtained by a process in which compounds, of the formula XXVII

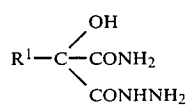 XXVII in which
R[1] has the meaning given above, are reacted with carbonyl compounds of the formula XXXII

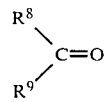 XXXII in which
R[8] and R[9] have the meaning given above.

12. Compounds of the formula XXXIII

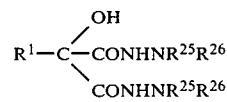 XXXIII in which
R[1] has the meaning given under 1,
R[25] represents hydrogen,
R[26] has the meanings given for R[23] and R[24] under processes 9 and 10 (above), or
R[25] and R[26] together represent the radical

wherein
R[8] and R[9] has the meaning given under 1, are obtained by a process in which the compounds of the formula XXXIV

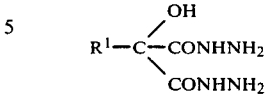 XXXIV are reacted with compounds of the formulae XXXIII, XXXV or XXXVII R[23]NCO(S) XXVIII; R[24]—A XXX; 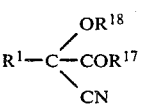 XXXII in which
A, R[23], R[24], R[8] and R[9] have the meanings given under 9, 10 and 11.

13. The compounds of the formula XII

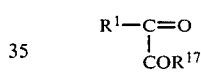 XII in which
R[1], R[18] and R[17] have the meaning given under 3 and 4, are obtained by a process in which compounds of the formula XXXV

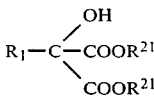 XXXV in which
R[1] and R[17] have the meaning given above, are reacted with HCN or compounds which donate HCN, or with trimethylsilyl cyanide.

14. The compounds of the formula XXI

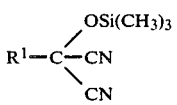 XXI in which
R[1] and R[21] have the meaning given under 6 and 8, are obtained by a process in which compounds of the formula XXV

 XXV in which
R[1] has the meaning given under 1, are reacted with alcohols of the formulae XXXVI

R[21]—OH  XXXVI in which
R[21] has the meaning given above, in the presence of inorganic mineral acids.

15. Compounds of the formula XXXVII

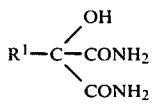

in which

R¹ has the meaning given under 1, are obtained by a process in which compounds of the formula XXV

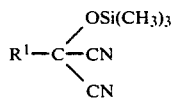

in which

R¹ has the meaning given above, are hydrolyzed with inorganic acids.

Compounds of the formula XXV

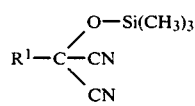

in which

R¹ has the meaning given under 1, are known and can be prepared by known processes (Chem. Ber. 106, page 87 (1977); Tetrahedron Letters No. 17, 1449–1450 (1973); and DE-OS (German Published Specification) No. 3,140,632).

Compounds of the formula XXXV

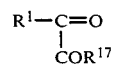

in which

R¹ and R¹⁷ have the meaning given under 13, are known. They are prepared in a manner which is in itself known (Tetrahedron Letters 1980, page 3539; Annalen (10) g, page 241; DE-OS (German Published Specification) No. 2,249,820 and DE-OS (German Published Specification) No. 2,708,189).

The active compounds are well tolerated by plants, have a favorable level of toxicity to warm-blooded animals, and are suitable for combating animal pests, especially insects, arachnida and nematodes, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example *Phylloxera vastatrix*, Pemphigus spp., *Pediculus humanus corporis*, Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable; for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating ectoparasites and endoparasites in the field of veterinary medicine.

The active compounds according to the invention are used in a known manner in the veterinary sector, such as by oral administration, for example in the form of tablets, capsules, drinks and granules, by dermal application, for example in the form of dipping, spraying, pouring on and spotting on, and dusting, and by parenteral administration, for example in the form of an injection.

EXAMPLE 1

144.5 g (0.55 mole) of 3,4-dichlorophenylhydroxymalonic acid diamide are suspended in 350 ml of thionyl chloride. The mixture is heated to the boil for 3 hours, while stirring, and cooled to 10° C., and the precipitated crystals are filtered off. The crystals are washed with diethyl ether, and dried at 50° C.

In this manner, 120.5 g (70.9% of theory) of 5-(3,4-dichlorophenyl)-5-aminocarbonyl-1,2,3-oxathiazolidin-4-one-2-oxide are obtained in the form of slightly yellowish crystals which melt between 191° and 192° C., with decomposition.

EXAMPLE 2

40.2 g (0.13 mole) of 5-(3,4-dichlorophenyl)-5-aminocarbonyl-1,2,3-oxathiadiazolidin-4-one-2-oxide are introduced into a freshly prepared solution of 7 g of sodium methylate in 200 ml of anhydrous methanol. After the mixture has been stirred for one hour at room temperature, the solvent is distilled off under reduced pressure, and the solid residue which remains is triturated with diethyl ether and dried at room temperature.

This procedure gives 43 g (100% of theory) of the sodium salt of 5-(3,4-dichlorophenyl)-5-aminocarbonyl-1,2,3-oxathiazolidin-4-one-2-oxide, which slowly decomposes at above 250° C., assuming a dark coloration.

EXAMPLE 3

31.2 g (0.2 mole) of ethyl iodide are added to a solution of 6.2 g (0.02 mole) of 5-(3,4-dichlorophenyl)-5-aminocarbonyl-1,2,3-oxathiazolidin-4-one-2-oxide and 2.02 g (0.02 mole) of triethylamine in 50 ml of acetonitrile. The solution is heated to the boil for four hours and then evaporated down under reduced pressure. The residue is taken up in 50 ml of dichloromethane, and the solution is washed with three times 20 ml of water. The organic phase is evaporated down and the residue is triturated with diethyl ether. In this manner, 4.7 g (70% of theory) of 3-ethyl-5-(3,4-dichlorophenyl)-5-aminocarbonyl-1,2,3-oxathiazolidin-4-one-2-oxide of melting point 127°-128° C. are obtained.

EXAMPLE 4

25 g (0.21 mole) of thionyl chloride are added to a suspension of 38 g (0.14 mole) of α-(4-chlorophenoxymethyl)-α'-tert.-butyl-hydroxy-acetamide in 140 ml of dichloromethane. The mixture is heated to the boil for twelve hours, while stirring. Thereafter, the solution is evaporated to dryness.

In this manner, 44.4 g (100% of theory) of 5-(4-chlorophenoxymethyl)-5-tert.-butyl-1,2,3-oxathiazolidin-4-one-2-oxide of melting point 132°-134° C. are obtained. After recrystallization from diethyl ether/petroleum ether, the melting point increases to 136°-137° C.

The following 1,2,3-oxathiazolidin-4-one-2-oxides are obtained analogously to Examples 1–4:

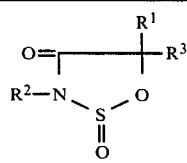

| Example No. | R$^1$ | R$^2$ | R$^3$ | Physical properties |
|---|---|---|---|---|
| 5 | t-butyl | H | CH$_2$Cl | M.p. 84–88° C. |
| 6 | t-butyl | H | CH$_2$—O—C$_6$H$_5$ | |
| 7 | t-butyl | H | CH$_2$—O—C$_6$H$_4$—F | M.p. 91–93° C. |
| 8 | t-butyl | H | CH$_2$—O—(2,3-Cl$_2$-C$_6$H$_3$) | M.p. 198–199° C. |
| 9 | t-butyl | H | CH$_2$—O—(2,4-Cl$_2$-C$_6$H$_3$) | M.p. 189° C. |
| 10 | t-butyl | H | CH$_2$—O—(2-Cl-4-F-C$_6$H$_3$) | M.p. 171° C. |
| 11 | C$_6$H$_5$ | H | CCl$_3$ | M.p. 113–116° C. |
| 12 | C$_6$H$_5$ | H | —CH$_2$—COOC$_2$H$_5$ | M.p. 136–137° C. |

-continued

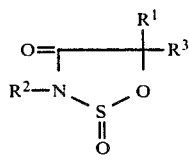

| Example No. | R¹ | R² | R³ | Physical properties |
|---|---|---|---|---|
| 13 | phenyl | H | —CH₂—O—(4-Cl-phenyl) | |
| 14 | phenyl | CH₃ | CONH₂ | M.p. 173–173.5° C. |
| 15 | phenyl | H | CONH₂ | M.p. 184–185° C. |
| 16 | 3,5-dichlorophenyl | H | CONH₂ | M.p. 223° C. |
| 17 | 3,4-dichlorophenyl | SCCl₂F | CONH₂ | viscous oil |
| 18 | 3,4-dichlorophenyl | ⁺N(C₂H₅) | CONH₂ | viscous oil |
| 19 | 3,4-dichlorophenyl | ⁺HN(morpholine)O | CONH₂ | M.p. 174° C. |
| 20 | 2,5-dichlorophenyl | C₂H₅ | CONH₂ | M.p. 135° C. Zos. |
| 20a | 4-CF₃-phenyl | CH₃ | CONH₂ | M.p. 174° C. |
| 20b | 4-CF₃-phenyl | C₂H₅ | CONH₂ | M.p. 136° C. |

-continued
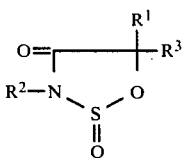
| Example No. | R¹ | R² | R³ | Physical properties |
|---|---|---|---|---|
| 20c | 3,4-diCl-phenyl | —CH₂—CH=CH₂ | $CONH_2$ | M.p. 116–117° C. |
| 20d | 3,4-diCl-phenyl | —CH(CH₃)₂ | $CONH_2$ | M.p. 136–138° C. |
| 21 | 3,4-diCl-phenyl | CH₃ | $CONH_2$ | M.p. 161–163° C. |
| 22 | 3,4-diCl-phenyl | —CH₂—C≡CH | $CONH_2$ | M.p. 167–168° C. |
| 23 | 3,5-diCl-phenyl | Na⊕ | $CONH_2$ | M.p. 260° C. |
| 24 | 2-Cl-5-CH₃-phenyl | H | $CONH_2$ | M.p. 198° C. |
| 25 | 4-CF₃-phenyl | H | $CONH_2$ | M.p. 178–179° C. |
| 26 | 2-Cl-5-NO₂-phenyl | H | $CONH_2$ | M.p. 184–185° C. |
| 27 | 2,3,5-triCl-phenyl | H | $CONH_2$ | M.p. 189° C. |

-continued
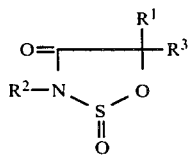
| Example No. | R¹ | R² | R³ | Physical properties |
|---|---|---|---|---|
| 28 | —CH₂—O—(phenyl) | H | CONH₂ | M.p. 201° C. |
| 28a | —(phenyl)—OCF₃ | H | CONH₂ | M.p. 178–179° C. |
| 28b | —(phenyl)—Cl | H | CONH₂ | M.p. 196° C. |
| 28c | —(phenyl with Cl, F, Cl) | H | CONH₂ | M.p. 228° C. |
| 28d | —CH₂—O—(phenyl with Br, F) | H | t-C₄H₉ | M.p. 180–181° C. |
| 28e | —CH₂—O—(phenyl with Cl, Cl, Cl) | H | t-C₄H₉ | M.p. 202–203° C. |
| 28f | —CH₂—SO₂—(phenyl) | H | t-C₄H₉ | M.p. 208° C. |
| 28g | —CH₂O—(phenyl)—Cl | CH₃ | t-C₄H₉ | $n_D^{20}$ 1.5330 |
| 28h | —CH₂O—(phenyl)—Cl | C₂H₅ | t-C₄H₉ | $n_D^{20}$ 1.5280 |
| 28i | —CH₂O—(phenyl)—Cl | —CH₂—C≡CH | t-C₄H₉ | $n_D^{20}$ 1.5404 |

-continued

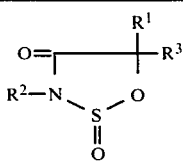

| Example No. | R¹ | R² | R³ | Physical properties |
|---|---|---|---|---|
| 28j | —CH₂—O—C₆H₃Cl₂ (3,4-diCl) | CH₃ | t-C₄H₉ | $n_D^{20}$ 1.5489 |
| 28k | —CH₂—O—C₆H₃Cl₂ (3,4-diCl) | C₂H₅ | t-C₄H₉ | $n_D^{20}$ 1.5400 |
| 29 | —CH₂—O—C₆H₃Cl₂ (3,4-diCl) | —CH₂—C≡CH | t-C₄H₉ | $n_D^{20}$ 1.5491 |
| 29a | —CH₂—O—C₆H₃Cl₂ (3,4-diCl) | —CH₂—C₆H₅ | t-C₄H₉ | M.p. 107–108° |
| 29b | —CH₂—O—C₆H₄Cl (4-Cl) | —CH₂—C₆H₅ | t-C₄H₉ | M.p. 91–92° |

EXAMPLE 30

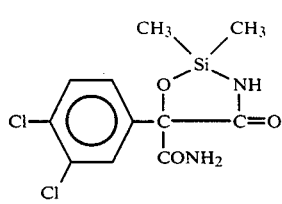

26.3 g of 3,4-dichlorophenylhydroxymalonic acid diamide were dissolved in 100 ml of warm absolute dioxane, and a solution of 11 g of dimethylsilyl dicyanide in 50 ml of absolute dioxane was then added. The mixture was heated under reflux for 8 hours, the cooling water temperature being 30° C., in order to separate off the hydrocyanic acid formed.

The mixture was then evaporated down, and the residue was boiled up with 250 ml of toluene. After the mixture had been cooled, the product was filtered off under suction. 28 g of 5-aminocarbonyl-5-(3,4-dichlorophenyl)-2-dimethyl-1-oxa-3-aza-2-sila-cyclopentan-4-one remained.

Melting point: 206°–207° C.

EXAMPLE 31

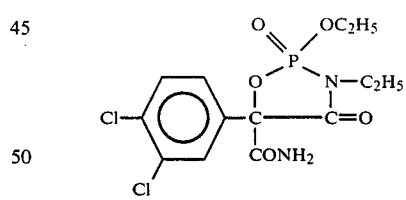

10.9 g of 3,4-dichlorophenylglyoxylic acid amide were dissolved in 200 ml of absolute dimethoxyethane, and a solution of 8.2 g of diethyl isocyanatophosphite in 10 ml of dimethoxyethane were added at 15° C. The solution was left to stand overnight at room temperature and then evaporated down. A further two portions of chloroform were added, and the solution was evaporated down, the final stage of this operation being carried out in a high vacuum at a bath temperature of 70° C. 20 g of a glassy residue remained, which was shown spectroscopically to be 2-ethoxy-3-ethyl-4-oxo-5-(3,4-dichlorophenyl)-1,3,2-oxazaphospholidin-5-aminocarbonyl-2-oxide.

The following compounds are prepared analogously to Examples 30 and 31:

| | R¹ | CONH₂ |
| :-- | :-- | :-- |
| | O= | |
| | R²—N | |
| | X—O | |

| Example No. | R¹ | R² | X |
| :-- | :-- | :-- | :-- |
| 32 | —⟨phenyl⟩-Cl, Cl | CH₃ | \Si(CH₃)₂/ |
| 33 | —⟨phenyl⟩-Cl, Cl | CH₃ | \P(=O)(OCH₃)/ |
| 34 | —⟨phenyl⟩ | CH₃ | \P(=O)(OCH₃)/ |

Preparation of the Precursors

EXAMPLE (a)

48.8 g (0.15 mole) of α-(4-chlorophenoxymethyl)-α'-tert.-butyl-trimethylsilyloxy-acetonitrile are stirred, in portions, into 110 ml of 96% strength sulphuric acid at 15°–20° C. The mixture is kept at this temperature for a further two hours, and is then poured onto ice and extracted with dichloromethane. The organic phase is washed with water, dried over anhydrous sodium sulphate and then evaporated to dryness. Trituration of the residue with diethyl ether, gives 20 g (49.4% of theory) of α-(4-chlorophenoxymethyl)-α'-tert.-butyl-hydroxyacetamide of melting point 160° C.

The following compounds are obtained analogously to Example (a):

a₁ α-(3,4-dichlorophenoxymethyl)-α'-t-butyl-hydroxyacetamide, m.p. 166° C.

a₂ α-(2-bromo-4-fluorophenoxymethyl)-α'-t-butyl-hydroxyacetamide, m.p. 116°–117° C.

a₃ α-(phenylsulphonylmethyl)-α'-t-butyl-hydroxyacetamide, m.p. 187°–188° C.

a₄ α-(2,4,5-trichlorophenoxymethyl)-α'-t-butyl-hydroxyacetamide, m.p. 145°–146° C.

a₅ α-(2,4-dichlorophenoxymethyl)-α'-t-butyl-hydroxyacetamide, m.p. 122°–123° C.

a₆ α-(4-chlorophenoxymethyl)-α'-t-butyl-hydroxyacetamide, m.p. 160° C.

a₇ α-(2,6-dichlorophenoxymethyl)-α-t-butyl-hydroxyacetamide, m.p. 169°–170° C.

a₈ α-(4-fluorophenoxymethyl)-α-t-butyl-hydroxyacetamide a₉ α-(2-chloro-4-fluorophenoxymethyl)-α-t-butyl-hydroxyacetamide a₁₀ α-(piperidinomethyl)-α'-t-butyl-hydroxyacetamide m.p. 106°–107° C.

a₁₁ α-(morpholinomethyl)-α'-t-butyl-hydroxyacetamide m.p. 103°–106° C.

a₁₂ α-(pyrazolinomethyl)-α'-t-butyl-hydroxyacetamide m.p. 138° C.

a₁₃ α-(propoxymethyl)-α'-t-butyl-hydroxyacetamide m.p. m.p. 106°–107° C.

a₁₄ α-(methoxymethyl)-α'-t-butyl-hydroxyacetamide m.p. 130°–131° C.

a₁₅ α-(ethoxymethyl)-α'-t-butyl-hydroxyaetamide m.p. 115°–116° C.

a₁₆ α-(propoxymethyl)-α'-t-butyl-hydroxyacetamide m.p. 124°–125° C.

a₁₇ α-chloromethyl-α'-t-butyl-hydroxyacetamide m.p. 123° C.

a₁₈ α-chloromethyl-α'-methylcyclohexyl-hydroxyacetamide, m.p. 80°–100° C.

a₁₉ α-bromomethyl-α'-(4-chlorophenyl)-hydroxyacetamide m.p. 108°–109° C.

a₂₀ α-(2,4-dichlorophenyl)-α'-chloromethyl-hydroxyacetamide, m.p. 137°–138° C.

a₂₁ α-(2,4-dichlorophenyl)-α'-bromomethyl-hydroxyacetamide, m.p. 138°–139° C.

EXAMPLE (b)

226.7 g (1 mole) of 1-(4-chlorophenoxy)-3,3-dimethylbutan-2-one are stirred, in portions, into a solution of 99.1 g (1 mole) of trimethylsilyl cyanide and 1 ml of triethylamine in 500 ml of dichloromethane. During this procedure, the temperature of the reaction mixture gradually increases to 30° C. The mixture is allowed to stand overnight at room temperature, the solvent is distilled off under reduced pressure and the crystalline residue which remains is triturated with a small amount of petroleum ether. In this manner, 280.9 g (86.2% of theory) of α-(4-chlorophenoxymethyl)-α'-tert.-butyl-trimethylsilyloxy-acetonitrile of melting point 98° C. are obtained.

The following compounds are obtained analogously to Example (b):

b₁ α-(2,4-dichlorophenoxymethyl)-α'-t-butyl-trimethylsilyloxy-acetonitrile, m.p. 94°–95° C.

b₂ α-phenoxymethyl-α'-t-butyl-trimethylsilyloxyacetonitrile, m.p. 61°–62° C.

b₃ α-(4-chlorophenoxymethyl)-α'-t-butyl-trimethylsilyloxy-acetonitrile, m.p. 98° C.

b₄ α-(3,4-dichlorophenoxymethyl)-α'-t-butyl-trimethylsilyloxy-acetonitrile, m.p. 90°–91° C.

b₅ α-(2,6-dichlorophenoxymethyl)-α'-t-butyl-trimethylsilyloxy-acetonitrile, m.p. 64°–65° C.

b₆ α-(4-fluorophenoxymethyl)-α'-t-butyl-trimethylsilyloxy-acetonitrile, m.p. 69° C.

b₇ α-(3-chlorophenoxymethyl)-α'-t-butyl-trimethylsilyloxy-acetonitrile, m.p. 109°–110° C.

b₈ α-(2,4,5-trichlorophenoxymethyl)-α'-t-butyl-trimethylsilyloxy-acetonitrile, m.p. 69°–70° C.

b₉ α-(2-chloro-4-fluorophenoxymethyl)-α'-t-butyl-trimethylsilyloxy-acetonitrile, m.p. 68° C.

b₁₀ α-(2-bromo-4-fluorophenoxymethyl)-α'-t-butyl-trimethylsilyloxy-acetonitrile, m.p. 47° C.

b₁₁ α-phenylsulphonylmethyl-α'-t-butyl-trimethylsilyloxy-acetonitrile, m.p. 121°–122° C.

EXAMPLE c

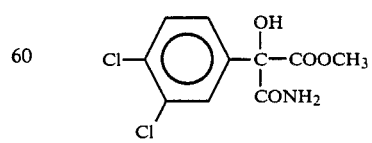

210 g of 3,4-dichlorophenyl-trimethylsilyloxymalonic acid ethyl ester nitrile were added dropwise to 400 g of sulphuric acid (96% strength) at a maximum of 40° C. Stirring was continued for a further hour at room temperature, and the mixture was then stirred into ice-water.

The precipitate, which was initially greasy but subsequently crystallized, was taken up in ethyl acetate, and the solution was washed, dried and evaporated down.

Recrystallization from isopropanol gave 3,4-dichlorophenyl-hydroxy-malonic acid methyl ester amide of melting point 132°–133° C.

EXAMPLE d

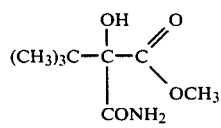

Analogously to the above example, 55 g of tert.-butylhydroxymalonic acid methyl ester amide were prepared from 187 g of tert.-butyl-trimethylsilyloxy-malonic acid methyl ester nitrile by hydrolysis in 500 g of $H_2SO_4$. Melting point 102°–103° C. (from petroleum ether).

EXAMPLE e

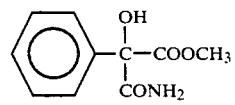

95 g of phenyl-hydroxy-malonic acid methyl ester nitrile were added dropwise to 500 g of $H_2SO_4$ at 30° C.

After stirring had been continued for 30 minutes at room temperature, the mixture was stirred into ice-water and taken up with methylene chloride, and the solution was washed and evaporated down. The residue was recrystallized from toluene. 72 g of phenyl-hydroxymalonic acid methyl ester amide of melting point 123°–4° C. were obtained.

EXAMPLE f

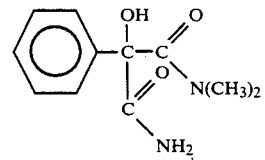

63 g of phenyltrimethylsilyloxymalonic acid dimethylamide nitrile were added dropwise to 250 ml of concentrated $H_2SO_4$ at 40° C. After the temperature had been kept at 40° C. for 9 hours while stirring, the mixture was poured onto ice and extracted with $CH_2Cl_2$, and the organic phase was worked up. 31 g of residue remained, and was recrystallized from i-propanol. 26.2 g of phenylhydroxymalonic acid amide dimethylamide remained; m.p. 137°–8° C.

EXAMPLE g

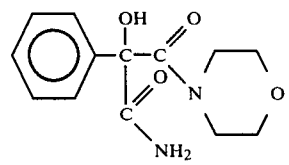

90 g of phenyltrimethylsilyloxymalonic acid morpholide nitrile were introduced into 300 ml of concentrated $H_2SO_4$ at a maximum of 40° C. After 2.5 hours at 40° C., the mixture was stirred into ice-water and extracted 3 times with methylene chloride. The organic phases were combined and washed with a small amount of water, and the solvent was distilled off, a high vacuum being applied in the final stage. 57 g of a glassy product remained, and this was identified spectroscopically as phenylhydroxymalonic acid morpholide amide.

EXAMPLE h

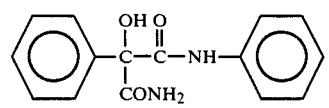

10 g of phenyltrimethylsilyloxymalonic acid anilide nitrile were introduced into 100 ml of concentrated hydrochloric acid at 30° C. The suspension was then heated to 50° C. for 2 hours, the residue was taken up in methylene chloride and the solution was washed and worked up. 5 g of a glassy crude product remained, and this was recrystallized from toluene. It was possible to isolate 4 g of phenylhydroxymalonic acid anilide amide. M.p. from 110° C., with decomposition.

EXAMPLE i

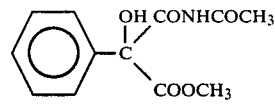

94 g of phenylhydroxymalonic acid methyl ester nitrile were added dropwise to a solution comprising 88.6 g of glacial acetic acid and 74 ml of concentrated $H_2SO_4$ at 40°–50° C. After 1 hour, the reaction solution was poured onto ice-water and extracted with methylene chloride. After the organic phase had been worked up, the residue was recrystallized from i-propanol. 50 g of a mixture of phenylhydroxymalonic acid methyl ester amide and phenylhydroxymalonic acid methyl ester acetamide were obtained in the approximate ratio 1:1, as determined from the spectroscopic data.

By treating the substance mixture with $NH_3$ in methanolic solution at 30°–50° C. for 2 hours, phenylhydroxymalonic acid diamide of melting point 159° C. was obtained.

EXAMPLE k

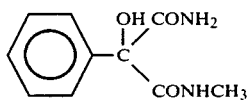

Methylamine was passed into a solution of 42 g of phenylhydroxymalonic acid methyl ester amide in 400 ml of methanol for 4 hours at the reflux temperature. After the mixture had been evaporated down, 30 g of phenylhydroxymalonic acid amide methylamide were obtained by recrystallization from ethanol (m.p. = 128° C.).

EXAMPLE l

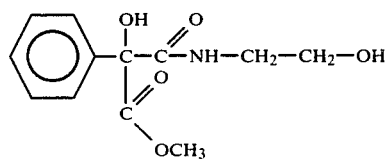

20.9 g of phenylhydroxymalonic acid methyl ester amide, 6.1 g of ethanolamine and 60 ml of methanol were heated under reflux for 8 hours. After the mixture had been evaporated down (in a high vacuum in the final stage), 24 g of highly viscous residue remained; this was identified spectroscopically as the desired phenylhydroxymalonic acid methyl ester β-hydroxyethylamide.

EXAMPLE m

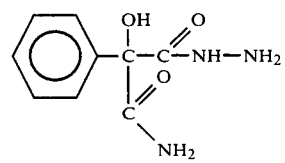

62.7 g of phenylhydroxymalonic acid methyl ester amide, 15 g of hydrazine hydrate and 200 ml of methanol were heated under reflux for 4 hours. The mixture was evaporated down at a bath temperature of up to 60° C. in the vacuum from a waterpump, toluene was added and the mixture was again evaporated down, this being done in a high vacuum in the final stage. 65 g of a glassy residue remained; this was shown spectroscopically to be phenylhydroxymalonic acid amide hydrazide.

EXAMPLE n

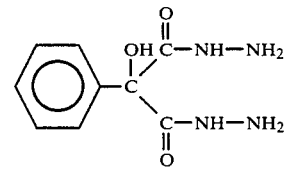

22.4 g of dimethyl phenylhydroxymalonate and 10 g of hydrazine hydrate in 100 ml of methanol were heated under reflux for 5 hours. Thereafter, the mixture was evaporated down at 50° C., in a high vacuum in the final stage. 24 g of a glassy residue remained, and this was recrystallized from water. 14 g of phenylhydroxymalonic acid bishydrazide of melting point 159° C. (decomposition) were obtained.

EXAMPLE o

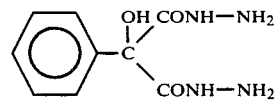

20.9 g of phenylhydroxymalonic acid methyl ester amide and 25 g of hydrazine hydrate in 150 ml of ethanol were heated under reflux for 12 hours. Thereafter, the mixture was evaporated down and the residue was recrystallized from 75 ml of water. 13 g of phenylhydroxymalonic acid bishydrazide of melting point 159° C. (decomposition) remained.

EXAMPLE p

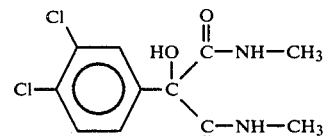

14.7 g of dimethyl 3,4-dichlorophenylhydroxymalonate were dissolved in 100 ml of methanol, and methylamine was passed in for 1 hour at 60° C. The mixture was evaporated down completely and the crystalline residue was recrystallized from 100 ml of ethanol. 12 g of 3,4-dichlorophenylhydroxymalonic acid dimethylamide (m.p. = 158°-60° C.) were obtained.

EXAMPLE q 3,4-Dichlorophenylhydroxymalonic acid dineopentylamide (m.p. = 94°-95° C.) were obtained analogously to the above method.

EXAMPLE r

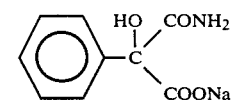

5.41 g of phenylhydroxymalonic acid methyl ester amide were stirred with 25.9 ml of aqueous 1N NaOH solution for 2.5 hours at room temperature. The reaction solution became virtually homogeneous during this procedure, and the pH value dropped to 6. After filtration, the solution was evaporated down, this being done in a high vacuum in the final stage. IR, NMR and MS (FAB) confirmed the presence of the monosodium salt of phenylhydroxymalonic acid monoamide.

EXAMPLE s

The free acid of the compound of Example s was obtained by suspending the salt from Example s in methylene chloride and treating the suspension with HCl gas.

EXAMPLE t

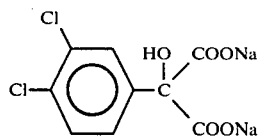

11.2 g of dimethyl 3,4-dichlorophenylhydroxymalonate were stirred with 76.6 ml of aqueous 1N NaOH solution at room temperature until the solution had a pH value of 6. The solution was then filtered, and the filtrate was evaporated down.

EXAMPLE u

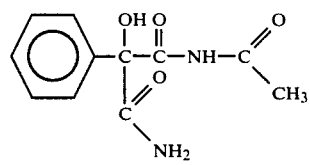

92 g of phenyltrimethylsilyloxymalonic acid dinitrile were added dropwise to a solution of 72 g of glacial acetic acid and 60 ml of concentrated $H_2SO_4$ at 40°–50° C. After 2 hours, the viscous solution was poured onto ice, the mixture was stirred thoroughly and the product was filtered off under suction. 53 g of crude product remained, and this was recrystallized from water. 40 g of phenylhydroxymalonic acid amide acetamide remained; m.p. 210° C. (decomposition).

EXAMPLE v

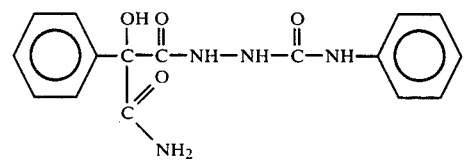

26.4 g of phenylhydroxymalonic acid amide hydrazide were dissolved in 50 ml of absolute dioxane, and a solution of 15 g of phenyl isocyanate in 15 ml of absolute dioxane was added. During this procedure, the temperature increased to 40° C., and a precipitate separated out. It was filtered off under suction after the mixture had been cooled, and the residue was boiled up with 500 ml of water. 27 g of not quite pure phenylhydroxymalonic acid amide (phenylaminocarbonyl)-hydrazide remained (m.p. 199° C.).

EXAMPLE w

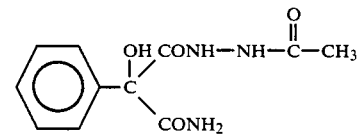

21.2 g of phenylhydroxymalonic acid amide hydrazide were dissolved in 100 ml of dioxane, 10.3 g of triethylamine were added and 8 g of acetyl chloride were added dropwise. Stirring was continued for 1 hour at room temperature, the precipitate was filtered off under suction and the mother liquor was evaporated down. 28 g of an impure crude product then remained; this was taken up in ethyl acetate, and the solution was washed with a small amount of water. After the solvent had been removed in a high vacuum at a bath temperature of 60° C., phenylhydroxymalonic acid amide acetyl hydrazide remained a glassy residue.

EXAMPLE x

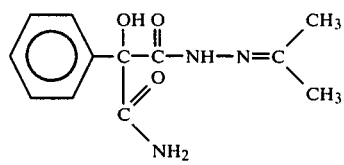

20 g of phenylhydroxymalonic acid amide hydrazide in 100 ml of acetone were heated under reflux for 3 hours. The crystals were filtered off under suction and recrystallized from ethanol. 15 g of phenylhydroxymalonic acid amide (2-propylidene)-hydrazide (m.p. 199°–201° C.) were obtained.

EXAMPLE y

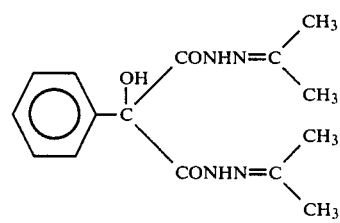

11.2 g of phenylhydroxymalonic acid bishydrazide in 100 ml of acetone were heated under reflux for 4 hours. The mixture was then evaporated down, this being done in a high vacuum in the final stage. 13.8 g of crude phenylhydroxymalonic acid bis-(2-propylidene-hydrazide) remained as a highly viscous residue.

EXAMPLE z

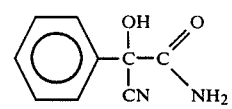

29.8 g of phenylglyoxylic acid amide were suspended in 30 ml of ethylene glycol dimethyl ether, 0.5 ml of triethylamine were added and replaced with 5.4 g of hydrocyanic acid. A homogeneous solution was formed. After the solvent had been removed, phenylhydroxymalonic acid amide nitrile remained.

EXAMPLE A

Plutella test
Solvent: 3 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified periods of time, the destruction in % is determined. 100% means that all the caterpillars have been killed; 0% means that none of the caterpillars have been killed.

In this test, for example, the following compounds from the preparation examples show a superior activity compared to the prior art: 2, 15, 24, 16, 1, 18, 19, 23, 3, 17, 22, 30 and 31.

EXAMPLE B

Tetranychus test (resistant)
Solvent: 3 parts by weight dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compounds from the preparation examples show a superior activity compared to the prior art: 14, 2, 16, 1, 18, 19, 23, 3, 17, 22 and 30.

EXAMPLE C

Test insect: *Phorbia antiqua* grubs (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l) being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compound from the preparation examples shows a superior action compared to the prior art: 24

EXAMPLE D

Test insect: Phaedon cochleariae
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is if practically no importance, only the amount by weight of active compound per unit volume of soil, which is given in ppm (=mg/l) being decisive. The treated soil is filled into pots and these planted with cabbage (Brassica oleracea). The active compound can in this way be taken up from the soil by the roots of the plants and be transported into the leaves.

To demonstrate the root-systemic effect, exclusively the leaves are infested with the above-mentioned test insects after 7 days. After a further 2 days, the evaluation is made by counting or estimating the dead insects. The root-systemic action of the active compound is deduced from the mortality figures. It is 100% if all the test animals have been killed and 0% if just as many test insects are still alive as in the case of the untreated control.

In this test, for example, the following compounds from the preparation examples show a superior action compared to the prior art: 16, 2, 18, 23, 19.

It will be appreciated that the instant specification and examples are set forth by way of illustration and not limitation, and that various modifications and changes may be made without departing from the spirit and scope of the present invention.

We claim:

1. A five-membered nitrogen-containing heterocyclic compound of the formula

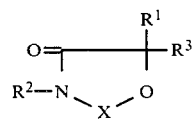

in which
X is S, SO or SO$_2$,
R$^1$ represents phenyl which can be optionally independently substituted by one or more of halogen, nitro, amino, OH, CN, C$_{1-4}$-alkyl, C$_{1-4}$-halogenoalkyl, C$_{1-4}$-alkoxy, methylenedioxy, ethylenedioxy, C$_{1-4}$-halogenoalkoxy, difluoromethylenedioxy or halogen-substituted ethylenedioxy, C$_{1-4}$-alkylthio, C$_{1-4}$-halogenoalkylthio, C$_{2-8}$-alkylsulphonyl, C$_{1-4}$-halogenoalkylsulphonyl, carboxyl, carbalkoxy, the radical C$_{1-4}$—alkoxy—N=CH—, or phenyl, phenoxy, phenylthio which can be optionally substituted by halogen or C$_{1-4}$-alkyl, or represents carboxyalkoxy having 2–4 C atoms, or
R$^1$ furthermore represents pyridinyl, pyrimidinyl, triazinyl, isoxazolyl, thiazolyl, oxadiazolyl, imidazolyl, triazolyl, furanyl or thienyl, which can be optionally mono- or polysubstituted by identical or different substituents from amongst halogen, C$_{1-4}$-alkyl, and C$_{1-4}$-alkoxy,
R$^2$ represents hydrogen, one equivalent of an alkali metal cation, alkaine earth metal cation or optionally substituted ammonium cation, $C_{1-6}$-alkyl, halogeno-$C_{1-6}$-alkyl, $C_{2-4}$-alkenyl or $C_{2-4}$-alkinyl, $R^3$ is $C_{1-7}$-alkyl optionally substituted by one or more of halogen, $C_{1-4}$-alkoxy, carboxyl, carbalkoxy, or phenyl, phenoxy or phenylthio, it being possible for the phenyl rings to be substituted by halogen or alkyl, or is —CO—$R^4$, $R^4$ is amino, alkylamino, arylamino, aralkylamino, dialkylamino, cycloalkylamino, alkenylamino, trialkylsilylamino, trialkylsilylalkylamino, nitrogen-containing saturated heterocyclic radicals which optionally contain further heteroatoms, or is —NHR$^7$, and $R^7$ is hydroxyl, formyl, alkylcarbonyl, alkenylcarbonyl, cycloalkenylcarbonyl or arylcarbonyl.

2. A compound according to claim 1 in which $R^1$ is phenyl which is optionally substituted by halogen, $C_{1-4}$-alkyl, $C_{1-4}$-alkoxy, $C_{1-4}$-halogenoalkoxy, $C_{1-4}$-halogenoalkyl, —NH$_2$, CH$_3$O—N=CH— or nitro, $R^2$ is hydrogen, $C_{1-6}$-alkyl, $C_{2-4}$-alkenyl, $C_{2-4}$-alkinyl or one equivalent of a sodium, potassium, calcium, ammonium or tri-($C_{1-4}$-alkyl)-ammonium cation, $R^3$ is $C_{1-4}$-alkyl, $C_{1-4}$-halogenoalkyl, or COR$^4$, and $R^4$ is amino or $C_{1-4}$-alkylamino.

3. A compound according to claim 1, in which $R^1$ is phenyl which is optionally one to tri substituted by identical or different substituents from amongst halogen, $C_{1-4}$-alkyl, nitro and $C_{1-4}$-alkoxy, $R^2$ is hydrogen, Na$^+$, $C_{1-4}$-halogenoalkyl, $C_{2-4}$-alkenyl or $C_{2-4}$-alkinyl, $R^3$ is $C_{1-4}$-alkyl, $C_{1-4}$-halogenoalkyl, or COR$^4$, and $R^4$ is amino.

4. A compound according to claim 1, in which $R^1$ is phenyl which is optionally substituted by chlorine, methyl, nitro or trifluoromethyl, $R^2$ is hydrogen, sodium, methyl, ethyl, propargyl or tri($C_{1-4}$-alkyl) ammonium, and $R^3$ is t-butyl, or COR$^4$, and $R^4$ is amino.

5. An insecticidal and acaricidal composition comprising an insecticidally and acaricidally effective amount of a compound according to claim 1 in admixture with a diluent.

6. A method of combatting insects and acarids which comprises administering to such insects and acarids or to a habitat thereof an insecticidally and acaricidally effective amount of a five-membered nitrogen-containing heterocyclic compound of the formula

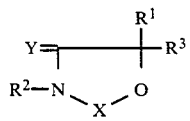

in which $R^1$ represents $C_{1-7}$-alkyl, $C_{2-7}$-alkenyl, $C_{3-7}$-cycloalkyl or $C_{5-8}$-cycloalkenyl, which can be optionally independently substituted by one or more of halogen, $C_{1-4}$-alkoxy, carboxyl, carbalkoxy, or phenyl, phenoxy or phenylthio, it being possible for the phenyl rings to be substituted by halogen or alkyl; or $R^1$ furthermore represents phenyl which can be optionally independently substituted by one or more of halogen, nitro, amino, OH, CN, $C_{1-4}$-alkyl, $C_{1-4}$-halogenoalkyl, $C_{1-4}$-alkoxy, methylenedioxy, ethylenedioxy, $C_{1-4}$-halogenoalkoxy, difluoromethylenedioxy or halogen-substituted ethylenedioxy, $C_{1-4}$-alkylthio, $C_{1-4}$-halogenoalkylthio, $C_{2-8}$-alkylsulphonyl, $C_{1-4}$-halogenoalkylsulphonyl, carboxyl, carboxyl, the radical $C_{1-4}$-alkoxy—N=CH—, or phenyl, phenoxy, Phenylthio which can be optionally substituted by halogen or $C_{1-4}$-alkyl, or represents carboxyalkoxy having 2–4 C atoms, or $R^1$ furthermore represents pyridinyl, pyrimidinyl, triazinyl, isoxazolyl, thiazolyl, oxadiazolyl, imidazolyl, triazolyl, furanyl or thienyl, which can be optionally mono- or polysubstituted by identical or different substituents from amongst halogen, $C_{1-4}$-alkyl, and $C_{1-4}$-alkoxy, $R^2$ represents hydrogen, one equivalent of an alkali metal cation, alkaline earth metal cation or optionally substituted ammonium cation, trialkylsilyl having 1–4 C atoms in the alkyl part, $C_{1-4}$-alkyl, $C_{1-4}$-alkylcarbonyl, phenyl or benzoyl, which can be optionally substituted by one or more of the following radicals (A), the substituents being identical or different:

(A) represents halogen, nitro, amino, CN, $C_{1-4}$-alkyl, $C_{1-4}$-halogenoalkyl, $C_{1-4}$-alkoxy, $C_{1-4}$-halogenoalkoxy, methylenedioxy, ethylenedioxy or difluoromethylenedioxy, halogen-substituted ethylenedioxy, $C_{1-4}$-alkylthio, $C_{1-4}$-halogenoalkylthio, $C_{2-8}$-alkoxyalkyl, $C_{2-8}$-halogenoalkoxyalkyl, $C_{1-5}$-alkylsulphenyl or phenylsulphenyl, $C_{1-4}$-alkylsulphonyl, $C_{1-4}$-halogenoalkylsulphonyl, carbalkoxy, the radical $C_{1-4}$-alkoxy—N=CH—, or phenyl, phenoxy or thiophenyl, which can be optionally substituted by halogen or by $C_{1-4}$-alkyl, or represents carboxyalkoxy having 2–4 C atoms, or $R^2$ furthermore represents $C_{1-4}$-alkoxycarbonyl, phenoxycarbonyl which can be optionally substituted by one or more of the radicals (A), $C_{1-4}$-alkylsulphonyl, phenylsulphonyl which can be optionally substituted by one or more of the radicals (A), $C_{1-4}$-alkylaminosulphonyl, $C_{1-5}$-alkylsulphenyl or phenylsulphenyl, di-$C_{1-4}$-alkylaminosulphonyl, phenylaminosulphonyl which can be optionally substituted by one or more of the radicals (A), phenyl-$C_{1-4}$-alkylaminosulphonyl or a radical of the formula

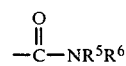

wherein $R^5$ and $R^6$ independently of one another represent hydrogen, $C_{1-20}$-alkyl, $C_{3-6}$-cycloalkyl, phenyl which can be optionally substituted by one or more of the radicals (A), phenylcarbonyl which can be optionally substituted by one or more of the radicals (A), $C_{1-10}$-alkylcarbonyl, $C_{1-4}$-alkylaminocarbonyl, $C_{1-10}$-alkoxycarbonyl, phenylaminocarbonyl or phenylsulphonyl, which can be optionally substituted by one or more of the radicals (A), $R^3$ represents the radicals stated for $R^1$, or also CN or the radical COR$^4$, $R^4$ represents amino, $C_{1-8}$-alkylamino or di-$C_{1-8}$-alkylamino, which can be optionally substituted by hydroxyl or $C_{1-4}$-alkoxy, phenylamino which can be optionally substituted by one or more of the radicals (A) given above, $C_{5-6}$-cycloalkylamino, a saturated heterocyclic structure having 5–6 C atoms in the ring, or a radical of the formula

—NHR⁷ wherein

R⁷ represents $C_{1-4}$-alkyl-carbonyl, $C_{2-4}$-alkenylcarbonyl, $C_{5-8}$-cycloalkenylcarbonyl, $C_{1-4}$-alkylamino, phenylamino which can be optionally substituted by one or more of the radicals (A) given above, $C_{1-4}$-alkylaminocarbonylamino

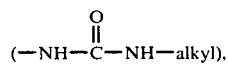
(—NH—C(=O)—NH—alkyl), phenylaminocarbonylamino

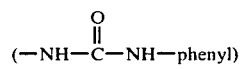
(—NH—C(=O)—NH—phenyl)

which can be optionally substituted by one or more of the radicals (A), $C_{1-4}$-alkylcarbonylamino

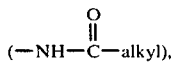
(—NH—C(=O)—alkyl), or benzoylamino which can be optionally substituted by one or more of the radicals (A); or R⁴ furthermore represents a radical of the formula

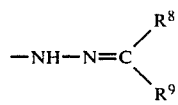

wherein

R⁸ represents $C_{1-4}$-alkyl, or phenyl which can be optionally substituted by one or more of the radicals (A), R⁹ represents hydrogen or $C_{1-4}$-alkyl, Y represents O and X represents SSO and $SO_2$, wherein R¹⁰ and R¹¹ represent $C_{1-4}$-alkyl.

* * * * *